(12) United States Patent
Straka et al.

(10) Patent No.: US 9,259,571 B2
(45) Date of Patent: Feb. 16, 2016

(54) ELECTRICAL STIMULATION THERAPY USING DECAYING CURRENT PULSES

(75) Inventors: Scott E. Straka, Ham Lake, MN (US); Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1447 days.

(21) Appl. No.: 12/603,316

(22) Filed: Oct. 21, 2009

(65) Prior Publication Data

US 2011/0093041 A1    Apr. 21, 2011

(51) Int. Cl.
*A61N 1/36*    (2006.01)
*A61N 1/08*    (2006.01)
*A61N 1/00*    (2006.01)

(52) U.S. Cl.
CPC .............. *A61N 1/08* (2013.01); *A61N 1/36125* (2013.01); *A61N 1/00* (2013.01)

(58) Field of Classification Search
CPC ............................. A61N 1/08; A61N 1/36125
USPC .......................................... 607/33, 60, 61, 62
See application file for complete search history.

(56) References Cited

U.S. PATENT DOCUMENTS

| | | | |
|---|---|---|---|
| 6,799,070 B2 | 9/2004 | Wolfe et al. | |
| 6,950,706 B2 | 9/2005 | Rodriquez et al. | |
| 6,988,006 B2 | 1/2006 | King et al. | |
| 7,450,987 B2 | 11/2008 | Varrichio et al. | |
| 7,483,747 B2 | 1/2009 | Gliner et al. | |
| 7,483,748 B2 | 1/2009 | Torgerson et al. | |
| 7,489,966 B2 | 2/2009 | Leinders et al. | |
| 2002/0055762 A1 | 5/2002 | Gliner | |
| 2003/0120310 A1* | 6/2003 | Mulhauser | 607/5 |
| 2003/0163166 A1* | 8/2003 | Sweeney et al. | 607/5 |
| 2003/0204221 A1* | 10/2003 | Rodriguez et al. | 607/48 |

(Continued)

FOREIGN PATENT DOCUMENTS

| | | |
|---|---|---|
| CN | 101126936 A | 2/2008 |
| CN | 101518667 A | 9/2009 |

(Continued)

OTHER PUBLICATIONS

U.S. Appl. No. 12/699,668, filed Feb. 3, 2010, entitled "Stimulation Mode Switching Based on Tissue Impendance Stability,".

(Continued)

*Primary Examiner* — Joseph Dietrich
(74) *Attorney, Agent, or Firm* — Shumaker & Sieffert, P.A.

(57) ABSTRACT

This disclosure describes generation of electrical stimulation pulses for electrical stimulation therapy. The stimulation pulses have a pulse current level and pulse width, and may be generated by a current regulator. The pulse voltage level may be a voltage level delivered by the current regulator while maintaining regulation of the pulse current level. During delivery of a pulse, a supply voltage level may decrease due to discharging of a supply capacitance, and the pulse voltage level may increase due to charging of a load capacitance. The pulse current level may be controlled to decrease during the pulse width such that a sum of the pulse voltage level and a headroom voltage of the current regulator does not exceed the supply voltage level. In some examples, the pulse may include sub-pulses with different sub-pulse current levels, where an earlier sub-pulse has a higher pulse current level than a later sub-pulse.

30 Claims, 14 Drawing Sheets

(56) References Cited

U.S. PATENT DOCUMENTS

| | | |
|---|---|---|
| 2003/0208244 A1 | 11/2003 | Stein et al. |
| 2005/0245977 A1 | 11/2005 | Varrichio et al. |
| 2005/0259454 A1 | 11/2005 | Varrichio et al. |
| 2008/0215125 A1 | 9/2008 | Farah et al. |
| 2009/0048643 A1 | 2/2009 | Erickson et al. |
| 2009/0132009 A1 | 5/2009 | Torgerson |

FOREIGN PATENT DOCUMENTS

| | | |
|---|---|---|
| WO | 03090849 A1 | 11/2003 |
| WO | 2004052451 A1 | 6/2004 |
| WO | 2009067292 A1 | 5/2009 |
| WO | 2010051062 A1 | 5/2010 |

OTHER PUBLICATIONS

U.S. Appl. No. 61/109,032, filed Oct. 28, 2008 entitled "Medical Devices and Methods for Delivery of Current-Based Electrical Stimulation Therapy,".

U.S. Appl. No. 12/579,036, filed Oct. 14, 2009 entitled "Medical Devices and Methods for Delivery of Current-Based Electrical Stimulation Therapy,".

U.S. Appl. No. 61/109,035, filed Oct. 28, 2008 entitled "Adaptable Current Regulator for Delivery of Current-Based Electrical Stimulation Therapy,".

U.S. Appl. No. 12/579,058, filed Oct. 14, 2009 entitled "Adaptable Current Regulator for Delivery of Current-Based Electrical Stimulation Therapy,".

U.S. Appl. No. 12/579,220, filed Oct. 14, 2009 entitled "Adaptable Current Regulator for Delivery of Current-Based Electrical Stimulation Therapy,".

U.S. Appl. No. 61/253,803, filed Oct. 21, 2009 entitled "Stimulation with Utilization of Case Electrode,".

U.S. Appl. No. 61/253,807, filed Oct. 21, 2009 entitled "Programming Techniques for Stimulation with Utilization of Case Electrode,".

International Search Report and Written Opinion for corresponding PCT Application No. PCT/US0210/048855, dated Dec. 13, 2010 (10 pgs.).

First Office Action from Chinese Counterpart Application No. 201080044984.3, dated Feb. 27, 2014, 23 pp.

* cited by examiner

ELECTRICAL STIMULATION THERAPY USING DECAYING CURRENT PULSES

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

A clinician selects values for a number of programmable stimulation parameters in order to define the electrical stimulation therapy to be delivered to a patient. For example, the clinician may select a current or voltage amplitude of the stimulation, and various characteristics of the stimulation waveform. In addition, the clinician may specify an electrode configuration used to deliver stimulation, including selected electrode combinations and electrode polarities. If the stimulation is delivered in the form of pulses, for example, the clinician may specify a current or voltage pulse amplitude, pulse width and pulse rate. A set of parameter values may be referred to as a stimulation program. A program group may include multiple programs. Multiple programs in a program group may be delivered on a simultaneous, time-interleaved, or overlapping basis.

SUMMARY

In general, this disclosure describes techniques for generation of electrical stimulation pulses for delivery of electrical stimulation therapy from a medical device, such as an implantable medical device, to a patient via one or more electrodes. The electrical stimulation pulses each have a pulse current level and pulse width. The pulse may be generated by a pulse generator that includes a current regulator, i.e., a regulated current source or sink. The current regulator is coupled to a supply voltage to deliver a pulse with a regulated current level. The pulse has a voltage level that may correspond to a voltage level that is delivered by the current regulator while maintaining substantial regulation of the pulse current level.

During delivery of a pulse, the supply voltage level may decrease due to discharging of a voltage supply capacitance, and the pulse voltage level may increase due to charging of a load capacitance. The pulse current level may be controlled to decrease during the pulse width such that a sum of the pulse voltage level and a headroom voltage level of the current regulator does not exceed a supply voltage level. In some examples, the pulse may include two or more sub-pulses with different sub-pulse current levels, where an earlier sub-pulse has a higher pulse current level than a later sub-pulse delivered for the given pulse.

In one example, the disclosure provides a method for delivery of electrical stimulation, the method comprising generating, with a current regulator, an electrical stimulation pulse having a pulse current level, a pulse voltage level, and a pulse width, controlling the pulse current level to decrease during the pulse width such that a sum of the pulse voltage level and a headroom voltage level of the current regulator does not exceed a supply voltage level, and delivering the pulse via one or more implantable electrodes.

In another example, the disclosure provides a medical device for delivery of electrical stimulation, the device comprising a stimulation pulse generator comprising a current regulator configured to generate an electrical stimulation pulse having a pulse current level, a pulse voltage level, and a pulse width, a controller configured to control the pulse current level to decrease during the pulse width such that a sum of the pulse voltage level and a headroom voltage level of the current regulator does not exceed a supply voltage level, and one or more implantable electrodes configured to deliver the pulse.

The details of one or more aspects of the disclosure are set forth in the accompanying drawings and the description below. Other features, objects, and advantages will be apparent from the description and drawings, and from the claims.

DETAILED DESCRIPTION

Figure 1:
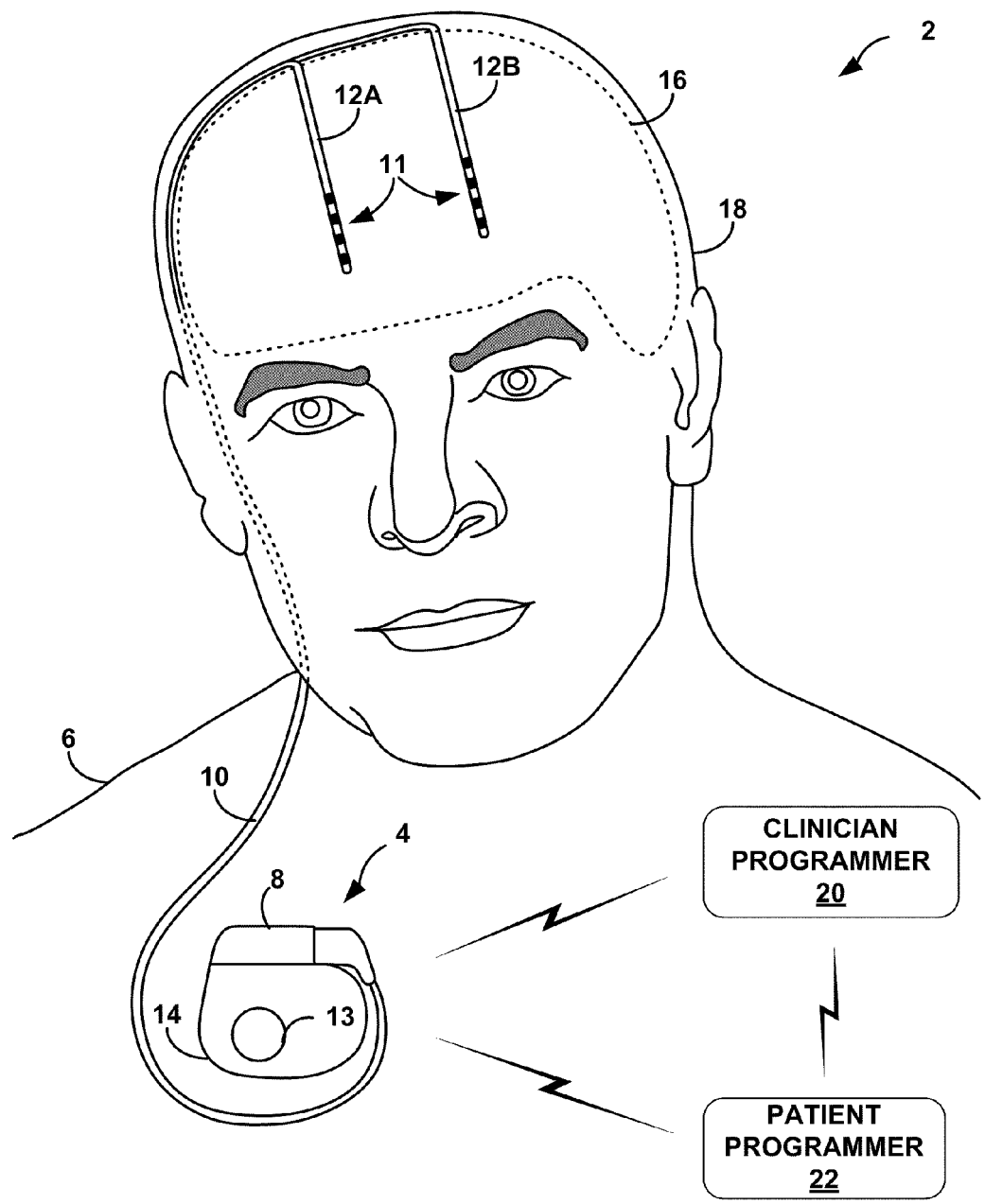
FIG. 1 is a conceptual diagram illustrating an example therapy system that includes an implantable stimulator coupled to an implantable stimulation lead.

This disclosure describes techniques for generation of electrical stimulation pulses for delivery of electrical stimulation therapy to tissue of a medical patient via one or more electrodes. An electrical stimulation pulse has a pulse current level, a pulse voltage level and a pulse width. The pulse may be generated by a pulse generator that includes a current regulator, i.e., a regulated current source or sink. The current regulator is coupled to a supply voltage to deliver a pulse with a regulated current level. The pulse voltage level is a voltage level that is delivered by the current regulator to maintain substantial regulation of the pulse current level.

During delivery of a pulse, the supply voltage level may decrease due to discharging of a voltage supply capacitance, and the pulse voltage level may increase due to charging of a load capacitance. The pulse voltage level that is necessary to maintain the regulated current pulse level may increase due to a voltage that builds up on the load capacitance. As described in this disclosure, the pulse current level may be controlled to decrease during the pulse width, from a higher current level to a lower current level, such that a sum of the pulse voltage level and a headroom voltage level of the current regulator does not exceed a supply voltage level.

A current regulator may have a headroom voltage level requirement that specifies a minimum voltage difference between the pulse voltage level and the supply voltage level. The headroom voltage level may correspond to an amount of voltage consumed by current regulator circuit components in producing a regulated current, and may be required to ensure proper operation of the current regulator. Hence, the pulse current level may be controlled to decrease during the pulse width such that a difference between the increasing pulse voltage level and the decreasing supply voltage level of the current regulator remains greater than the headroom voltage level.

The controlled decrease in the stimulation current pulse, in some examples, may be based at least in part on the decrease in the supply voltage level over the pulse width. The voltage supply for the current regulator may store charge on a capacitor module to produce the supply voltage level. For example, the capacitor module may use different numbers of capacitors on a selective basis to produce a desired supply voltage level. The capacitors may be selectively switched to form a capacitor stack with a supply capacitance sufficient to produce the supply voltage. As a pulse is delivered, however, the supply capacitance discharges, causing a decrease in the supply voltage level.

In some examples, the controlled decrease in the regulated stimulation current pulse may be based at least in part on an increase in a load voltage during the pulse width. The pulse is delivered to a biological tissue load via an electrically conductive path between the current regulator and one or more electrodes. The conductive path may include one or more series capacitors, such as capacitors used for recharge, that present a series capacitance to the current regulator. The electrode-tissue interface may present an additional series capacitance. In combination, these capacitances form a load capacitance that can build up charge during delivery of a current pulse, producing a load voltage. As the load voltage increases, the amount of pulse voltage level that is necessary to maintain the regulated pulse current level increases.

As the supply voltage level discharges and the pulse voltage level increases, it is possible that the sum of the pulse voltage level and the headroom voltage level could exceed the supply voltage level. In this case, the increase in the pulse voltage level may cause the pulse current level to go out of regulation. As described above, to promote reliable regulation, the pulse current level may be controlled to decrease during the pulse width such that reliable current regulation can be maintained. The pulse current level may be controlled to decrease based at least in part on the decrease in the supply voltage level during the pulse width, the increase in the load voltage (and resulting increase in the pulse voltage level) during the pulse width, or both.

As an example, the pulse current level may decrease according to a decay profile that could correspond to a linear slope, a nonlinear curve, a piecewise series of sub-pulses with progressively decreasing current levels, or other shapes. In each case, known or measured capacitances of the load and the voltage supply can be utilized to find a desirable curve-fit for the shape of the regulated current pulse in order to prevent the sum of the pulse voltage level and headroom voltage level from exceeding the supply voltage level. In general, the pulse may have a higher current level at the beginning than at the end of the pulse, allowing a higher average current to be delivered in a controlled manner without needing to increase the required initial supply voltage.

The decrease in the supply voltage level during delivery of the regulated current pulse, in combination with the increase in the pulse voltage level due to the increasing load voltage, can adversely impact the performance of the current regulator. To prevent loss of regulation, the initial supply voltage level stored on the supply capacitor could be increased. However, an increase in the supply voltage level may require an implantable medical device to include larger or more numerous capacitors in a voltage supply, resulting in decreased efficiency, increased size and/or increased cost. Increased size due to additional capacitors or larger capacitors may be especially undesirable for an implantable medical device (IMD). The generation of a pulse current level that decreases over its pulse width may permit delivery of larger current levels for a given supply voltage, or the use of smaller supply voltages for a given pulse current level.

As less pulse current is delivered, less pulse voltage is needed than otherwise would be needed to deliver the same current for a given load impedance. In this manner, by reducing the pulse current level during the pulse width, the amount of the increase in the pulse voltage level can be reduced such that a sum of the pulse voltage level and a headroom voltage level of the current regulator does not exceed the supply voltage level, ensuring that regulation of the pulse current level can be maintained during the pulse width. Yet, in some examples, a desired average pulse current level still may be delivered. The current pulse may be controlled to start at a higher current level at the beginning of the pulse width and decrease toward a lower current level at the end of the pulse width.

A higher average current can be delivered in a controlled manner without the need to increase the supply voltage level. It may be possible to deliver a desired average current with substantially the same total charge while requiring less initial supply voltage to be stored on a capacitor module associated with the voltage supply. The ability to use a lower supply voltage to deliver pulses may permit longer battery life or longer time between recharges in the case of a rechargeable battery, as well as minimal or no effect on therapeutic outcome. In some cases, the voltage supply may permit the use of downsized capacitors to generate the required pulse voltage, allowing electrical hybrid circuitry to be smaller, possibly permitting smaller devices and/or larger batteries for a given device size.

In some cases, the pulse may be formed as a split pulse comprising first and second sub-pulses. The second sub-pulse follows the first sub-pulse in time during the pulse width. The first and second sub-pulses may fit within the pulse width of the split pulse. The second sub-pulse follows the first sub-pulse in time and has a pulse current level that is less than the pulse current level of the first sub-pulse. In this sense, the pulse may be split into two portions: a higher current portion and a lower current portion. In other cases, the pulse may comprise more than two sub-pulses, such as high, medium and low portions, or a greater number of sub-pulses with even greater granularity in current level. In general, the proportion of the higher current level or levels to the lower current level or levels in the split pulse may be determined based on the decrease in the supply voltage level and the increase in the load voltage over the pulse width, to maintain the necessary headroom voltage between the pulse voltage level and the supply voltage level as they increase and decrease, respectively.

The stimulation pulses may be delivered using various electrode arrangements such as unipolar arrangements, bipolar arrangements or multipolar arrangements. A unipolar stimulation arrangement generally refers to the use of an anode on the housing that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one ore more anodes on a lead that source current and multiple cathodes on the same lead or another lead that sink current. A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

In some implementations, each electrode may be driven by a respective current regulator that selectively sinks or sources current at a specified current level. Hence, a stimulation generator may comprise a plurality of current regulators coupled to respective electrodes. The current regulators may be selectively activated and controlled to deliver current to tissue of the patient via the electrodes. Selected anodes may source amounts of regulated current that approximately equal amounts of regulated current sunk by selected cathodes. In some implementations, one or more anodes or cathodes may be coupled to source or sink unregulated current relative to a voltage supply rail or reference voltage. For regulated current pulses, a decaying pulse profile may be used, as described above, in order to prevent the pulse voltage level from exceeding a level at which the difference between the pulse voltage level and the supply voltage level would be less than the applicable headroom voltage level for the current regulator, thereby maintaining regulation of the pulse current level.

Electrical stimulation current pulses may be delivered to implantable electrodes by a stimulation pulse generator associated with an implantable medical device (IMD). Alternatively, the stimulation pulse generator may be associated with an external medical device. In either case, the implantable electrodes may be deployed via one or more implantable leads. For example, one or more fully implantable leads may be coupled to an IMD housing implanted within the patient. In this case, one or more electrodes may be provided on the IMD housing, as well as on one or more leads. Alternatively, one or more percutaneously implantable leads may be coupled to an external medical device housing positioned outside of the patient.

FIG. 1 is a conceptual diagram illustrating an example system 2 that may be used to deliver stimulation therapy to patient 6. Patient 6 ordinarily, but not necessarily, will be a human. Generally, therapy system 2 includes an IMD in the form of an implantable stimulator 4 that delivers electrical stimulation to patient 6 via one or more implantable electrodes. The implantable electrodes may be deployed on one or more implantable medical leads, such as implantable medical lead 10, and, in some cases, on an electrode on the housing of implantable stimulator 4. The electrical stimulation may be in the form of regulated stimulation current pulses having a controlled pulse current level.

Various parameters of the stimulation current pulses may be defined by a stimulation program. The stimulation current pulses may be delivered substantially continuously or in bursts, segments, or patterns, and may be delivered alone or in combination with pulses defined by one or more other stimulation programs. Although FIG. 1 shows a fully implantable stimulator 4, as mentioned above, techniques described in this disclosure may be applied to external stimulators having electrodes deployed via percutaneously implantable leads. Also, as discussed above, one or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. Stimulator 4 generates programmable electrical stimulation, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts an example housing, or can, electrode 13. Housing electrode 13 may be formed integrally with an outer surface of hermetically-sealed housing 14 of implantable stimulator 4, also referred to in this disclosure as an implantable medical device (IMD), or otherwise coupled to housing 14. In some examples, housing electrode 13 is defined by an uninsulated portion of an outward facing portion of housing 14 of implantable stimulator 4. Other divisions between insulated and uninsulated portions of housing 14 may be employed to define two or more housing electrodes, which may be referred to as case or can electrodes. In some examples, housing electrode 13 comprises substantially all of housing 14, or a portion of the housing 14. Housing electrode 13 typically may comprise an anode, although the housing electrode could be formed as a cathode in some cases.

Using the techniques of this disclosure, one or more electrodes 11 may deliver stimulation current pulses having current levels that are controlled to decrease during the pulse width such that a sum of the pulse voltage level and a headroom voltage level of the current regulator does not exceed the supply voltage level for the current regulator. In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to implantable stimulator 4. In the example of FIG. 1, lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one or more regions of brain 16, which may be selected based on patient condition or disorder.

Implantable stimulator 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 16 may include the pedunculopontine nucleus (PPN), thalamus, basal ganglia structures (e.g., globus pallidus, substantia nigra, subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation pulse parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage pulse amplitude (i.e., level), pulse width and pulse rate. Patient 6 may also select a program, e.g., from among a plurality of stored programs, as the present program to control delivery of stimulation by implantable stimulator 4, or select different program groups.

Clinician programmer 20 or patient programmer 22 may be configured to define a stimulation pulse current level profile based on a desired stimulation pulse current level. The profile may define, for example, a linear slope, a nonlinear curve, a piecewise series of sub-pulses with progressively decreasing current levels, or other shapes, and may be selected to decrease the pulse current level during the pulse width such that a sum of the pulse voltage level and a headroom voltage level of the current regulator does not exceed a supply voltage level. In some examples, an average of the pulse current level may be selected such that the sum of the pulse voltage level and the headroom voltage level does not exceed the supply voltage level. The programmer 20 or 22 may define the decay profile based on data relating to the voltage levels associated with a voltage supply for a current regulator used by stimulator 4 to deliver stimulation current pulses, including a supply voltage decrease and a load voltage increase during the pulse width. Hence, the pulse decay profile may be defined by a programmer. Alternatively, the programmer 20 or 22 may simply specify a desired pulse current level. In this case, stimulator 4 may be configured to receive the desired pulse current level and generate the current pulse decay profile to decrease the pulse current level during the pulse width such that a sum of the pulse voltage level and a headroom voltage level of the current regulator does not exceed a supply voltage level.

In some examples, implantable stimulator 4 delivers stimulation according to a group of programs at a given time. Each program of such a program group may include respective values for each of a plurality of therapy parameters, such as respective values for each of current pulse level (i.e., amplitude), pulse width, pulse rate and electrode configuration (i.e., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other, or other devices, using any of a variety of local wireless communication techniques, such as RF communication according to the 802.11 or Bluetooth specification sets, infrared communication, e.g., according to the IrDA standard, or other standard or proprietary telemetry protocols. Clinician programmer 20 and patient programmer 22 may each include a transceiver to permit bi-directional communication with stimulator 4. Programmers 20, 22 may also communicate with another programming or computing device via exchange of removable media, such as magnetic or optical disks, or memory cards or sticks. Further, programmers 20, 22 may communicate with implantable stimulator 4 and other programming devices via remote telemetry techniques known in the art, communicating via a local area network (LAN), wide area network (WAN), public switched telephone network (PSTN), or cellular telephone network, for example.

The shapes of the pulses delivered by system 2 may vary according to different design objectives. In accordance with some examples of this disclosure, the current level of at least some pulses may be shaped, i.e., controlled, to decrease during the pulse width such that a sum of the pulse voltage level and a headroom voltage level of the current regulator does not exceed the supply voltage level. In this manner, regulation of the current level may be maintained. Again, in some cases, this feature may permit the use of a voltage supply with smaller capacitors to produce the supply voltage. In particular, the initial supply voltage may be made lower without compromising regulator performance.

Implantable stimulator 4 regulates current that is sourced or sunk by one or more electrodes, referred to as regulated electrodes. In some examples, one of the electrodes may be unregulated. In such configurations, either the housing electrode or a lead electrode may be the unregulated electrode. A source current may refer to a current that flows out of an electrode, e.g., from a regulated current source via a regulated current path to surrounding tissue, or from a reference voltage via an unregulated current path. A sink current may refer to a current that flows into an electrode, e.g. from surrounding tissue and is sunk by a regulated current sink via a regulated current path or by a reference voltage via an unregulated current path.

An anode may source current, whereas a cathode may sink current. Hence, an anodic electrode delivers source current while a cathodic electrode delivers sink current. Regulated source currents may sum to produce a greater overall source current. Regulated sink currents may sum to produce a greater overall sink current. Regulated source and regulated sink currents may partially or entirely cancel one another. In the case of partial cancellation, the source and sink currents may produce a net difference in the form of a net source current or sink current. If provided, an unregulated current path can source or sink current in amounts approximately equal to this net difference.

Figure 2:
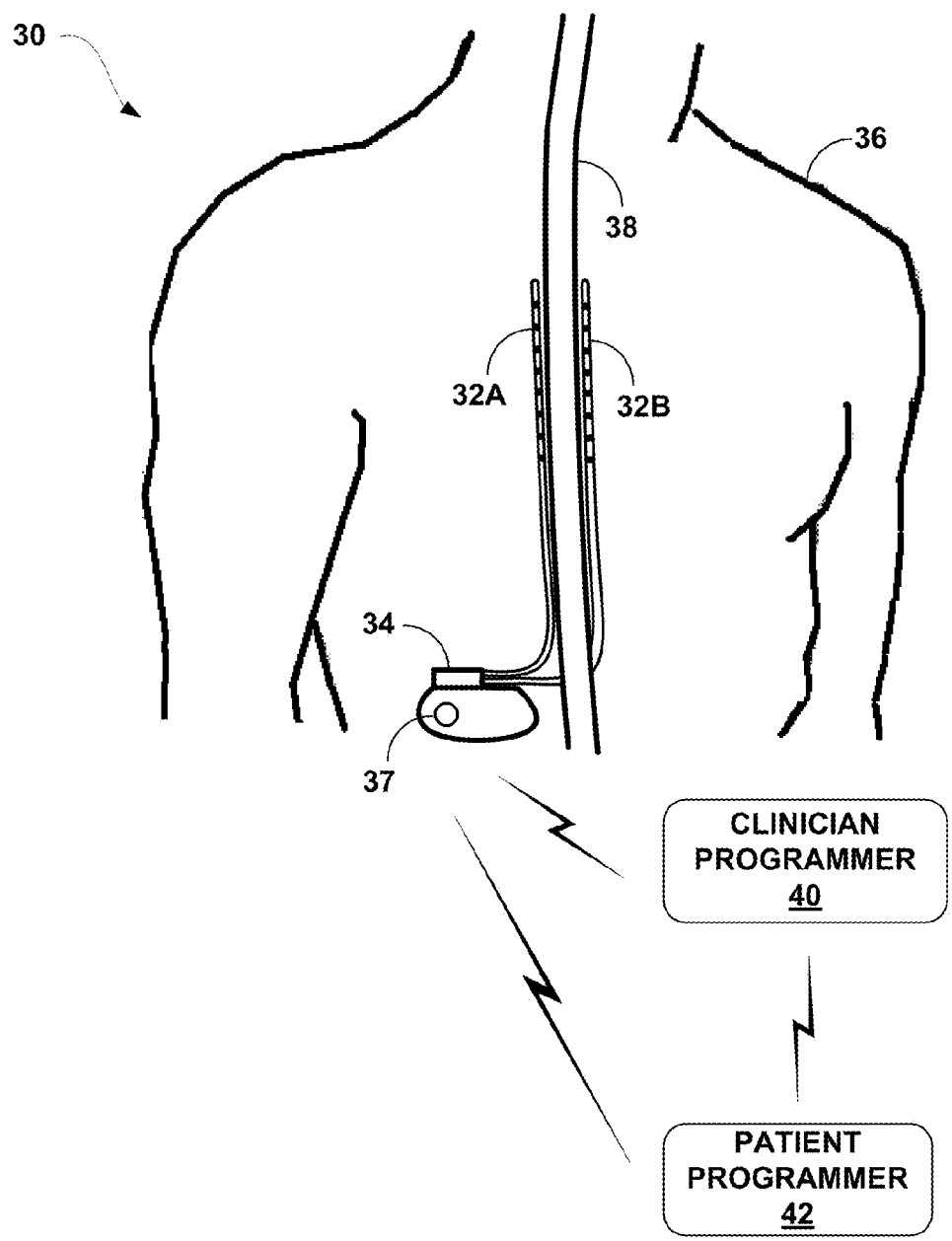
FIG. 2 is a conceptual diagram illustrating another example therapy system that includes an implantable stimulator coupled to implantable stimulation leads.

FIG. 2 is a conceptual diagram illustrating a system 30 that delivers stimulation therapy to spinal cord 38 of patient 36. Like FIG. 1, FIG. 2 represents another example of an electrical stimulation system that may support stimulation techniques described in this disclosure. In the example of FIG. 2, system 30 is configured to deliver stimulation therapy from implantable stimulator 34 to spinal cord 38 of patient 36 via a combination of one or more electrodes (not shown) carried by, i.e., located on, implantable medical leads 32A and 32B (collectively "leads 32") as well as the housing of implantable stimulator 34, e.g., housing electrode 37. Other electrical stimulation systems may be configured to deliver electrical stimulation to gastrointestinal organs, pelvic nerves or muscle, peripheral nerves, or other stimulation sites.

System 30 and, more particularly, implantable stimulator 34 may operate in a manner substantially similar to implantable stimulator 4 (FIG. 1). That is, implantable stimulator 34 delivers controlled current stimulation pulses to patient 36 via one or more regulated, stimulation electrodes. The current level for each pulse may be controlled to decrease during the pulse width such that a sum of the pulse voltage level and a headroom voltage level of the current regulator does not exceed a supply voltage level. For example, the pulse current level may decrease according to a decay profile comprising a linear slope, a nonlinear curve, a piecewise series of sub-pulses with progressively decreasing current levels, or other shapes. The decay profile may be determined based on a decrease in the supply voltage level during the pulse width, and/or an increase in a load voltage during the pulse width, which may cause a corresponding increase in the pulse voltage during the pulse width.

In the example of FIG. 2, the distal ends of leads 32 carry electrodes that are placed adjacent to the target tissue of spinal cord 38. The proximal ends of leads 32 may be both electrically and mechanically coupled to implantable stimulator 4 either directly or indirectly via a lead extension and header. Alternatively, in some examples, leads 32 may be implanted and coupled to an external stimulator, e.g., through a percutaneous port. In additional example implementations, stimulator 34 may be a leadless stimulator with one or more arrays of electrodes arranged on a housing of the stimulator rather than leads that extend from the housing. Application of certain techniques will be described in this disclosure with respect to implantable stimulator 34 and implantable leads 32 having ring electrodes for purposes of illustration. However, other types, shapes or configurations of electrodes may be used.

Stimulator 34 may be implanted in patient 36 at a location minimally noticeable to the patient. For SCS, stimulator 34 may be located in the lower abdomen, lower back, or other location to secure the stimulator. Leads 32 are tunneled from stimulator 34 through tissue to reach the target tissue adjacent to spinal cord 38 for stimulation delivery. At the distal ends of leads 32 are one or more electrodes (not shown). In some examples, for a unipolar or omnipolar arrangement, electrodes at the distal ends of leads 32 may transfer the stimulation pulses from the lead to the tissue (or from the tissue to a lead) substantially simultaneously with stimulation pulses delivered via a housing electrode, e.g., electrode 37. Some of the electrodes may be electrode pads on a paddle lead, circular (i.e., ring) electrodes surrounding the body of leads 32, conformable electrodes, cuff electrodes, segmented electrodes, or any other type of electrodes capable of forming unipolar, bipolar or multi-polar electrode configurations.

Implantable stimulator 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by implantable stimulator 34 may take the form of stimulation current pulses defined by stimulation pulse current levels, pulse widths and pulse rates, with at least some pulses having a decay profile selected based on a supply voltage level decrease and a load voltage increase during the pulse width, as described above. Stimulation may be delivered via selected combinations of electrodes located on one or both of leads 32 and on the housing. Stimulation of spinal cord 38 may, for example, prevent pain signals from traveling through the spinal cord and to the brain of patient 34. Patient 34 may perceive the interruption of pain signals as a reduction in pain.

With reference to FIG. 2, a user, such as a clinician or patient 36, may interact with a user interface of external clinician programmer 40 or patient programmer 42 to program stimulator 34. Programming of stimulator 34 may refer generally to the generation and transfer of commands, programs, or other information to control the operation of the stimulator. For example, each programmer 40, 42 may function in a manner similar to programmers 20, 22, respectively, of FIG. 1 to transmit programs, parameter adjustments, program selections, group selections, or other information to control the operation of stimulator 34, e.g., by wireless telemetry. In general, clinician programmer 40 may support selection and generation of programs by a clinician for use by stimulator 34, whereas patient programmer 42 may support adjustment and selection of such programs by a patient during ordinary use.

Programmers 40, 42, like programmers 20, 22 of FIG. 1, may be configured to communicate with stimulator 34, each other, or other devices via wireless communication. Programmers 40, 42 may communicate, for example, via wireless communication with implantable stimulator 34 using radio frequency (RF) telemetry techniques known in the art. Programmers 40, 42 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmers 40, 42 may also communicate with another programming or computing device via exchange of removable media, such as magnetic or optical disks, or memory cards or sticks. Also, programmers 40, 42 may communicate with implantable stimulator 4 and other programming devices via remote telemetry techniques known in the art, communicating via a local area network (LAN), wide area network (WAN), public switched telephone network (PSTN), or cellular telephone network, for example.

Figure 3:
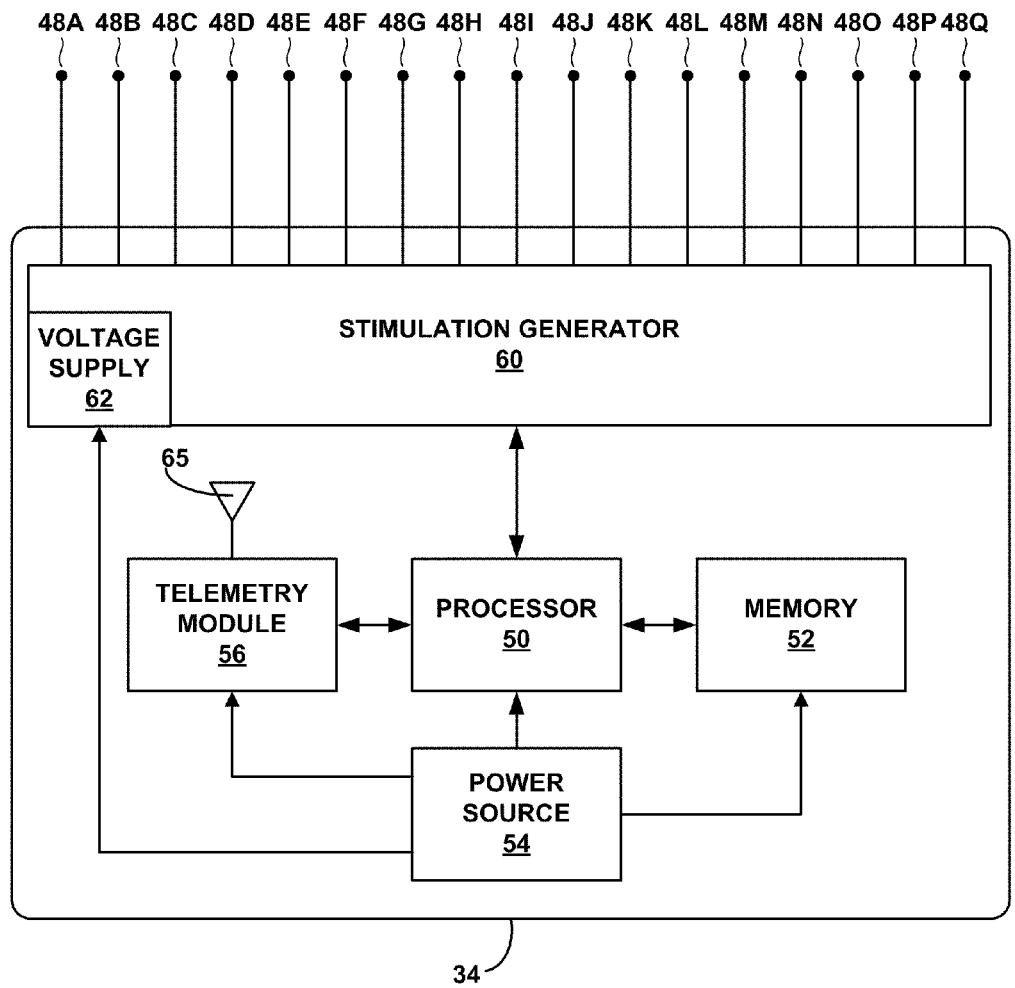
FIG. 3 is a block diagram illustrating various example components of an implantable electrical stimulator.

FIG. 3 is a block diagram illustrating various components of an example implantable stimulator 34 in system 30. Although the components shown in FIG. 3 are described in reference to implantable stimulator 34 for purposes of illustration, the same or similar components may also be included within other stimulators, such as implantable stimulator 4 shown in FIG. 1 and used within system 2. Also, in some cases, the components of FIG. 3 may be implemented in an external stimulator. In the example of FIG. 3, implantable stimulator 34 includes processor 50, memory 52, power source 54, telemetry module 56, antenna 65, and a stimulation generator 60. Implantable stimulator 34 is also shown in FIG. 3 coupled to electrodes 48A-Q (collectively "electrodes 48").

Electrodes 48A-48P are implantable and may be deployed on one or more implantable leads. With respect to FIG. 1, lead segments 12A and 12B may carry electrodes 48A-H and electrodes 48I-P, respectively. In some cases, one or more additional electrodes, such as electrode 48Q, may be located on or within the housing of implantable stimulator 34, e.g., to provide a common or ground electrode or a housing anode or cathode. With respect to FIG. 2, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with implantable stimulator 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), two leads with four electrodes each (2×4), three leads with four electrodes each (3×4), three leads with eight electrodes each (3×8), three leads with four, eight, and four electrodes, respectively (4-8-4), or other configurations. Different electrodes are selected to form electrode combinations. Polarities are assigned to the selected electrodes to form electrode configurations.

Electrode 48Q represents one or more electrodes that may be carried on a housing, i.e., can, of implantable stimulator 34. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of implantable stimulator 34, such as stimulation generator 60, processor 50, memory 52, telemetry module 56, and power source 54.

Memory 52 may store instructions for execution by processor 50, stimulation therapy data, sensor data, and/or other information regarding therapy for patient 6. Processor 50 may control stimulation generator 60 to deliver stimulation according to a selected one or more of a plurality of programs or program groups stored in memory 52. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 4 in this disclosure.

Processor 50 may include one or more microprocessors, digital signal processors (DSPs), application-specific integrated circuits (ASICs), field-programmable gate arrays (FPGAs), or other digital logic circuitry. Processor 50 controls operation of implantable stimulator 34, e.g., controls stimulation generator 60 to deliver stimulation therapy according to a selected program or group of programs retrieved from memory 52. For example, processor 50 may control stimulation generator 60 to deliver electrical signals, e.g., as stimulation pulses or continuous waveforms, with pulse current amplitudes (i.e., levels), pulse widths (if applicable), and pulse rates specified by one or more stimulation programs. As described in this disclosure, the pulse current level may be controlled to decrease during the pulse width such that a sum of the pulse voltage level and a headroom voltage level of the current regulator does not exceed the supply voltage level. Processor 50 may also control stimulation generator 60 to selectively deliver the stimulation via subsets of electrodes 48, also referred to as electrode combinations, and with polarities specified by one or more programs.

Upon selection of a particular program group, processor 50 may control stimulation generator 60 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate, if applicable. In some cases, for a continuous waveform, parameters may include amplitude and frequency. In addition, each program may specify a particular electrode combination for delivery of stimulation, and an electrode configuration in terms of the polarities of the electrodes. The electrode combination may specify particular electrodes in a single array or multiple arrays, and on a single lead or among multiple leads.

Stimulation generator 60 is electrically coupled to electrodes 48A-P via conductors of the respective lead, such as lead 12 in FIG. 1 or leads 32 in FIG. 2, in implementations in which electrodes 48A-P are carried by, located on, leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads of the IMD.

Stimulation generator 60 may include stimulation generation circuitry to generate stimulation pulses and circuitry for switching stimulation across different electrode combinations, e.g., in response to control by processor 50. Each electrode 48A-48Q may be coupled to a respective source and/or sink within stimulation generator 60, such that the current levels sourced or sunk via the electrodes may be individually and selectively controlled. Stimulation generator 60 produces electrical stimulation pulses in accordance with one or more programs based on control signals from processor 50. In accordance with some examples of this disclosure, a program may specify that pulse current levels should be controlled to decrease during the pulse width with a particular slope or shape such that a sum of the pulse voltage level and a headroom voltage level of the current regulator does not exceed the supply voltage level. In some examples, the current pulse may be formed to have a slope or shape that is determined based on a decrease in the supply voltage level, an increase in a load voltage level, or both, during the pulse width.

Stimulation generator 60 may include a voltage supply 62 having a charging circuit and a capacitor module. The charging circuit of voltage supply 62 may selectively apply energy from power source 54 (FIG. 3) to the capacitor module for generation and delivery of a supply voltage at a desired supply voltage level for use by a current regulator in generation of stimulation signal. For example, each current regulator may be coupled to the same supply voltage or separate supply voltages generated by voltage supply 62 across the capacitor module. In addition to capacitors, the capacitor module may include switches to selectively adjust the number of capacitors used in a capacitor stack to produce the supply voltage level. Using capacitors and switches, for example, a capacitor module associated with voltage supply 62 may be configurable, e.g., based on signals from processor 50, to store a desired voltage level that provides a supply voltage level to a current regulator for delivery of stimulation pulses at a controlled current amplitude (i.e., current level) specified by a program. In some examples, for delivery of stimulation pulses, switches within the capacitor module also may control the widths of the pulses based on signals from processor 50.

An electrode combination selected for delivery of stimulation current may comprise an anode on the IMD housing and one or more cathodes on a lead. In other examples, the electrode combination may include multiple anodes and/or multiple cathodes on one or more leads. Hence, in various cases, the electrode combination may be bipolar, unipolar, or multipolar. In each case, one or more current regulators may be used to deliver current pulses with controlled current levels via at least some of the electrodes. In a particular electrode combination, each active electrode (i.e., each electrode selected for delivery of stimulation) may be coupled to a current regulator to source or sink a regulated current pulse. Alternatively, in some cases, one or more active electrodes may be coupled to a current regulator while one or more other active electrodes are coupled to an unregulated current path, e.g., to a supply voltage or a reference voltage.

Telemetry module 56 may include a radio frequency (RF) transceiver to permit bi-directional communication between implantable stimulator 34 and each of clinician programmer 40 and patient programmer 42. Telemetry module 56 may include an antenna 65. Antenna 65 may be formed, for example, by a conductive coil or wire embedded in a housing associated with medical device 34. Alternatively, antenna 65 may be mounted on a circuit board carrying other components of implantable stimulator 34 or take the form of a circuit trace on the circuit board. Telemetry module 56 may permit communication with clinician programmer 20 and patient programmer 22 in FIG. 1 or clinician programmer 40 and patient programmer 42 in FIG. 2, to receive, for example, new programs or program groups, or adjustments to programs or program groups.

Power source 54 may include a non-rechargeable primary cell battery or a rechargeable battery and may be coupled to power circuitry. However, the disclosure is not limited to examples in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 4 or 34. In some examples, power requirements may be small enough to allow stimulator 4 or 34 to utilize patient motion at least in part and implement a kinetic energy-scavenging device to trickle charge a rechargeable battery.

Power source 54 may include a voltage converter, such as a DC-DC voltage converter, that converts the battery voltage to one or more voltages at different voltage levels. Voltage supply 62 may receive one of the voltages from power source 54 and use the voltage to generate a supply voltage for stimulation generator 60. As discussed above, an array of capacitors and switches may be configured to convert the voltage from power source 54 into a supply voltage. For example, voltage supply 62 may use the voltage from power source 54 to charge the voltage supply capacitor module to provide a supply voltage at a desired level to one or more current regulators. In particular, current regulators within stimulation generator 60 may use the supply voltage to generate stimulation current pulses at desired current levels.

During delivery of a current pulse, as described above, the supply capacitor module may be partially discharged from an initial supply voltage level to a decreased supply voltage level. Voltage supply 62 may recharge the supply capacitor module to the initial supply voltage level, e.g., between successive pulses. In this manner, the supply voltage on the supply capacitor module at the beginning of each pulse may be recharged up to the initial supply voltage level. At the end of delivery of each pulse, the supply voltage on the supply capacitor module may drop to a decreased supply voltage level due to discharge of the supply capacitance. As described in this disclosure, stimulation generator 60 may be configured to control the stimulation pulse current level to decrease during the pulse width such that a sum of the pulse voltage level and a headroom voltage level of the current regulator does not exceed the supply voltage level, thereby maintaining substantial regulation of the pulse current level.

In some examples, voltage supply 62 may generate a high supply voltage for use by regulated current sources and/or a low supply voltage for use by regulated current sinks. The high supply voltage may be a positive voltage and the low supply voltage may be a negative voltage. A stimulation pulse may deliver cathodic current in the case of a current sink or anodic current in the case of a current source. In either case, the magnitude of the stimulation pulse voltage could exceed the applicable supply voltage provided by voltage supply 62 in the sense that the absolute value of the pulse voltage is greater than the absolute value of the applicable supply voltage. For example, if the high supply voltage is +12 volts, the pulse voltage from a current source could exceed the high supply voltage if the pulse voltage is greater than +12 volts. If the low supply voltage is −12 volts, the pulse voltage from a current sink could exceed the low supply voltage if the pulse voltage is less than −12 volts. In each case, the magnitude of the pulse voltage is greater than the absolute value of the applicable supply voltage.

Figure 4:
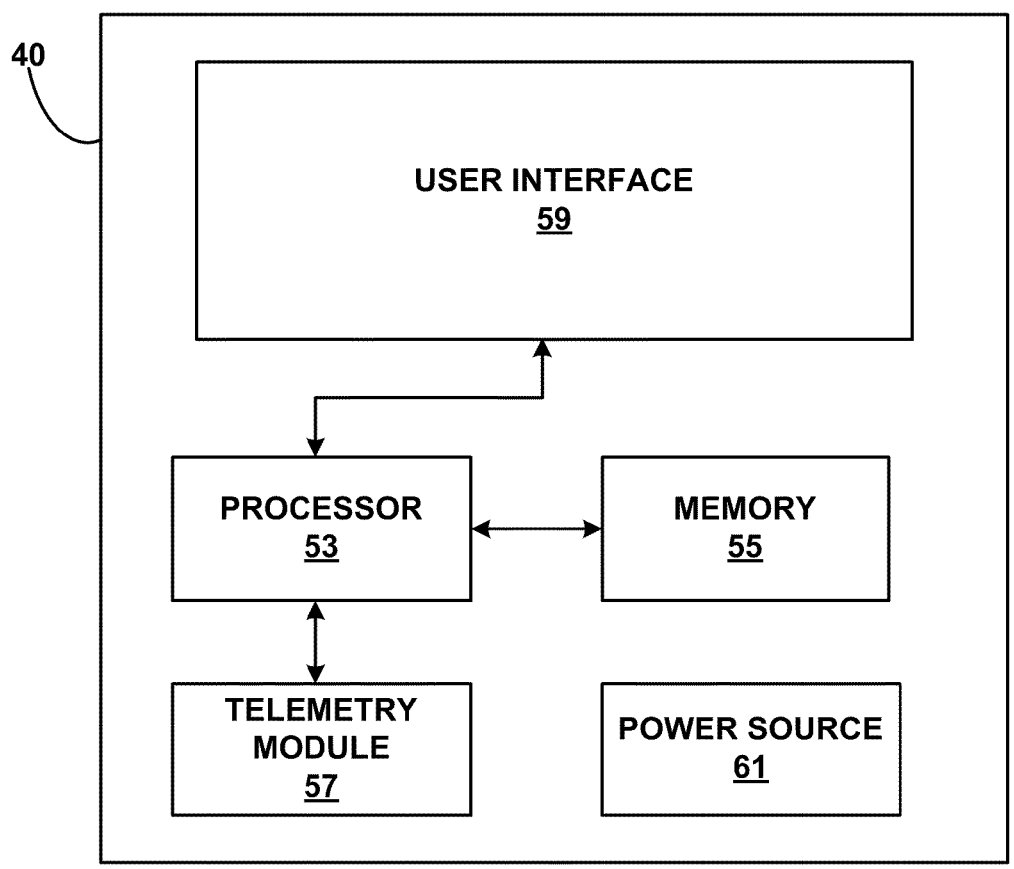
FIG. 4 is a block diagram illustrating various example components of an external programmer for use with an electrical stimulator.

FIG. 4 is a functional block diagram illustrating various components of an external programmer 40 for an implantable stimulator such as stimulator 4 (FIG. 1) or stimulator 34 (FIG. 2). Although the components shown in FIG. 4 are described in reference to external programmer 40 (FIG. 2), some or all of the components may also be included within clinician programmer 20 or patient programmer 22 as shown in FIG. 1, or patient programmer 42 as also shown in FIG. 2. As shown in FIG. 4, external programmer 40 includes processor 53, memory 55, telemetry module 57, user interface 59, and power source 61. In general, processor 53 controls user interface 59, stores and retrieves data to and from memory 55, and controls transmission of data with implantable stimulator 34 through telemetry module 57. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 48 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. Memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 4 or 34, such as therapy delivery values.

A clinician or patient 36 interacts with user interface 59 in order to, for example, manually select, change or modify programs, adjust voltage or current amplitude, provide efficacy feedback, or view stimulation data. User interface 59 may include a screen and one or more input buttons that allow external programmer 40 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 57 allows the transfer of data to and from stimulator 34 (or stimulator 4 in FIG. 1). Telemetry module 57 may communicate automatically with stimulator 34 at a scheduled time or when the telemetry module detects the proximity of the stimulator. Alternatively, telemetry module 57 may communicate with stimulator 34 when signaled by a user through user interface 59. To support RF communication, telemetry module 57 may include appropriate electronic components, such as amplifiers, filters, mixers, encoders, decoders, and the like.

Programmer 40 may communicate wirelessly with implantable stimulator 34 using, for example, RF communication or proximal inductive interaction. This wireless communication is possible through the use of telemetry module 57 which may be coupled to an internal antenna or an external antenna. Telemetry module 57 may be similar to telemetry module 56 of implantable stimulator 34 (FIGS. 2 and 3).

Programmer 40 may also be configured to communicate with another computing device via wireless communication techniques, or direct communication through a wired, e.g., network, connection. Examples of local wireless communication techniques that may be employed to facilitate communication between programmer 40 and another computing device include RF communication based on the 802.11 or Bluetooth specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

Figure 5:
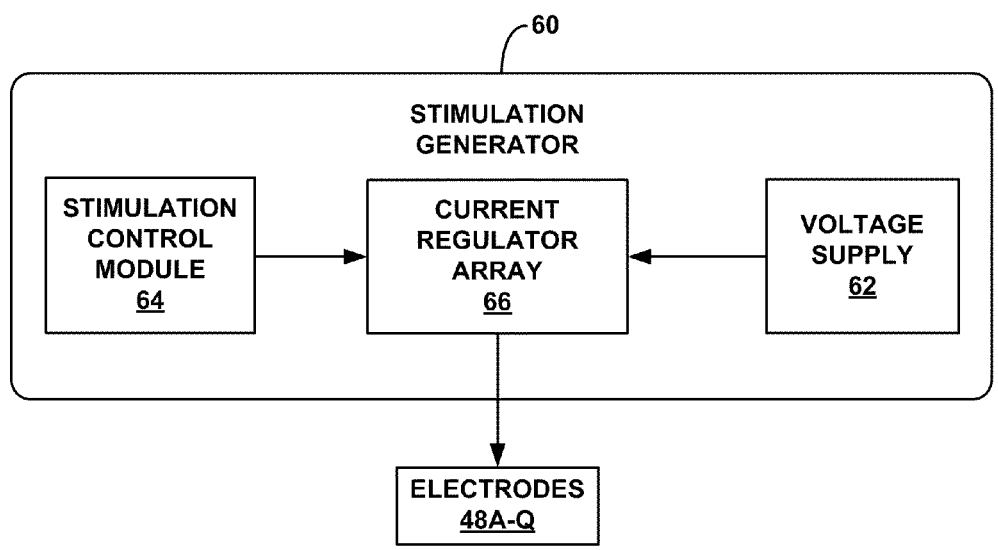
FIG. 5 is a block diagram illustrating various components of an example electrical stimulation generator for use in the implantable electrical stimulator of FIG. 3.

FIG. 5 is a block diagram illustrating various components of an example stimulation generator 60. Stimulation generator 60 may be used with an implantable stimulator, e.g., to perform the functions of stimulation generator 60 as described with reference to FIGS. 1-3. Although described with respect to implantable stimulator 34, stimulation generator 60 may also be used for implantable stimulator 4, or other types of stimulators. In the example of FIG. 5, stimulation generator 60 is selectively configured, e.g., based on instructions from processor 50 (FIG. 3), to deliver controlled current stimulation pulses to patient 36 via various electrode combinations. In the example illustrated in FIG. 5, stimulation generator 60 includes voltage supply 62, stimulation control module 64, and current regulator array 66.

Voltage supply 62 may receive operating power from power source 54 (FIG. 3). In turn, voltage supply 62 may provide a supply voltage to the current regulators in current regulator array 66. Voltage supply 62 may provide a high supply voltage ($V_{HIGH}$) and a low supply voltage ($V_{LOW}$). The high supply voltage may be coupled to a regulated current source as a supply voltage. The low supply voltage may be coupled to a regulated current sink as a supply voltage. Again, the supply voltage level may be the voltage level used by the current regulator to maintain regulation of the pulse current level, and may decrease during the delivery of a pulse due to discharge of the supply capacitance.

The high and low supply voltages may be positive and negative voltages, respectively, supplied by voltage supply 62. As discussed above, the high supply voltage $V_{HIGH}$ may be used as a high reference voltage level for a current source, and the low supply voltage $V_{LOW}$ may be used as a low reference voltage level for a current sink. As an example, in some implementations, $V_{HIGH}$ may have a voltage level of approximately +12 V to +20 V, and $V_{LOW}$ may have a voltage level of approximately −12 V to −20 V. The values of $V_{HIGH}$ and $V_{LOW}$ may vary during operation, e.g., drop from an initial value as a stimulation pulse is delivered and then be recharged to the initial value for delivery of the next pulse. If the stimulation current pulse has a pulse voltage with a magnitude that, when summed with the magnitude of the headroom voltage, exceeds $V_{HIGH}$ in the case of a current source, or exceeds $V_{LOW}$ in the case of current sink, the current level of the stimulation current pulse may be not be adequately regulated.

Stimulation control module 64 forms a stimulation controller that controls current regulator array 66 to source and sink regulated current stimulation pulses via selected combinations of electrodes 48A-48Q. Stimulation control module 64 may include one or more microprocessors, microcontrollers, digital signal processors (DSPs), application-specific integrated circuits (ASICs), field-programmable gate arrays (FPGAs), or other integrated or discrete logic circuitry. In operation, stimulation control module 64 may control delivery of electrical stimulation according to one or more programs that specify stimulation parameters such as electrode combination, electrode polarity, stimulation current pulse amplitude, pulse rate, and/or pulse width. Programs may be defined by a user via an external controller and downloaded to an implantable stimulator 4 or 34 for use by stimulation control module 64.

Current regulator array 66 includes a plurality of regulated current sources and sinks, each of which may be coupled to a respective electrode. A current regulator may function as either a current source or sink, e.g., by including a source and sink in parallel or by otherwise being selectively configurable to operate as either a source or a sink. For convenience, however, the term "current regulator" may be used in this disclosure to refer generally to either a source or sink. Hence, each of the current regulators in current regulator array 66 may operate as a regulated current source that delivers stimulation via a corresponding one of electrodes 48A-Q or a regulated current sink that receives current from a corresponding one of electrodes 48A-Q, where electrodes 48A-48Q may be provided on leads, on a stimulator housing, on a leadless stimulator, or in other arrangements. In general, electrodes 48A-48Q may be referred to below as electrodes 48 for conciseness.

Each current regulator of current regulator array 66 may be selectively activated to source or sink current via an electrode 48 coupled to the regulator, in which case the electrode is considered active, or deactivated to provide a high impedance connection for the electrode, in which case the electrode may be considered inactive. Hence, each electrode 48 may function as a regulated anode or regulated cathode by connection to a regulated current source or regulated current source, or function as a high impedance node that may not source or sink a significant amount of current. In addition, in some implementations, one or more electrodes 48 may be selectively coupled to a high or low supply voltage (e.g., $V_{HIGH}$ or $V_{LOW}$ from voltage supply 62) by switches, instead of via current regulators, providing an unregulated current path to a high or low supply voltage to source or sink current, respectively. In some examples, stimulation control module 64 selectively activates current regulators in current regulator array 66 to configure electrodes 48 in unipolar, bipolar or multipolar electrode configurations.

In some examples, pulse widths and pulse rates may be selectively controlled by stimulation control module 64 by selectively activating current regulators in current regulator array 66, e.g., on a pulse-by-pulse basis, at selected times and for selected durations. In addition, stimulation control module 64 may selectively control individual regulated current sources or sinks in current regulator array 66 to deliver stimulation current pulses via the selected electrodes with desired current levels. In particular, as described in this disclosure, stimulation control module 66 may be configured to control the pulse current levels delivered by individual current regulators to decrease during the pulse width such that a sum of the pulse voltage level and a headroom voltage level of the current regulator does not exceed the supply voltage level.

As discussed above, stimulation control module 64 also may deactivate the current regulators of current regulator array 66 that are tied to inactive electrodes, i.e., electrodes that are not active as regulated electrodes in a given electrode configuration. For example, each current regulator of current regulator array 66 may include an internal enable switch controlled by stimulation control module 64 that disconnects voltage supply 62 from the current regulator or otherwise disables the current regulator when the corresponding electrode is not used by stimulation generator 60 as a regulated electrode to deliver stimulation, e.g., as indicated by a stimulation program that indicates which electrodes are active to define a given electrode combination.

Figure 6:
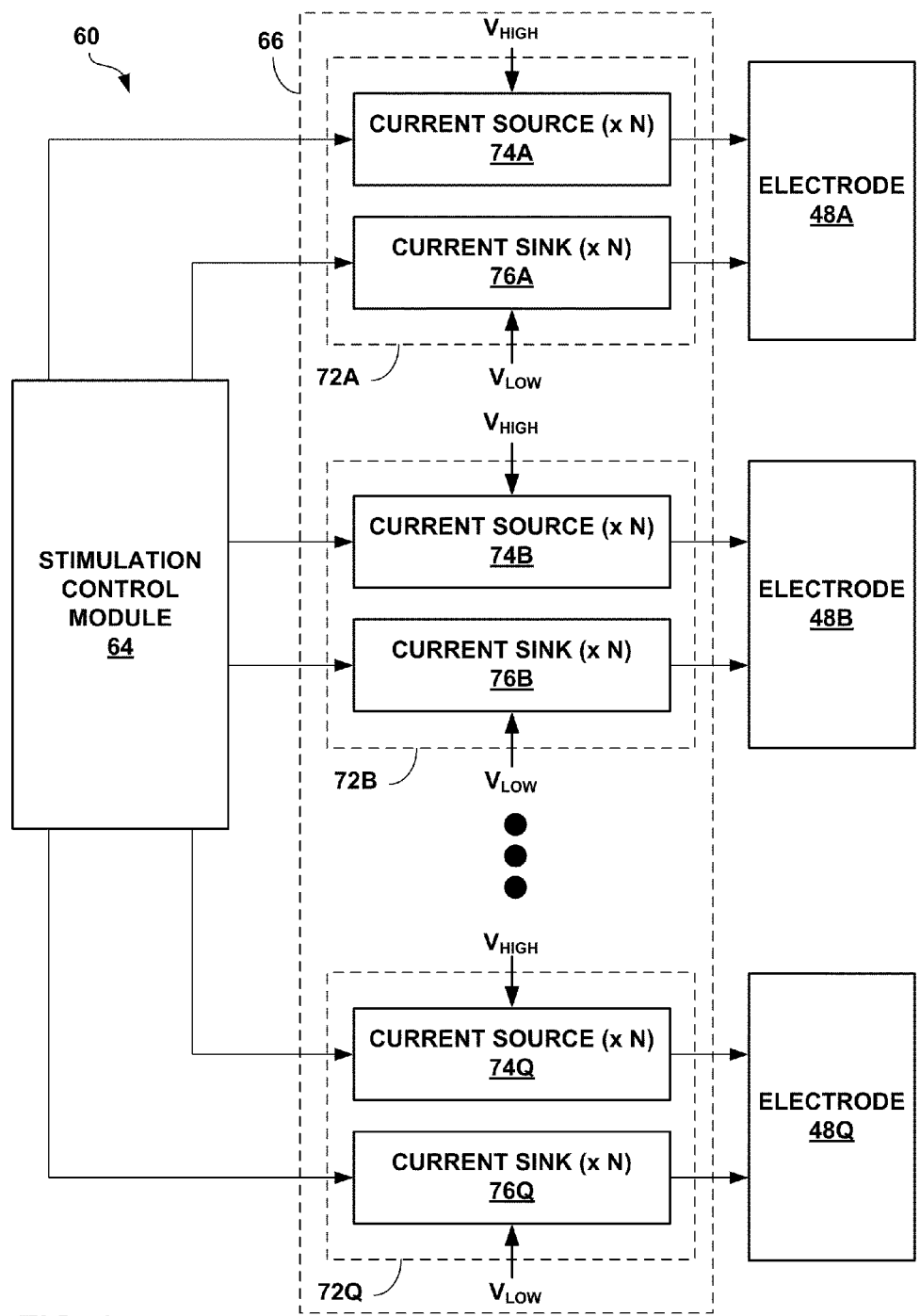
FIG. 6 is a block diagram illustrating the example stimulation generator of FIG. 5 in greater detail.

FIG. 6 is a block diagram illustrating an example of various components of stimulation generator 60A shown in FIG. 5 in greater detail. In particular, FIG. 6 shows current regulator array 66 in greater detail. As shown in FIG. 6, current regulator array 66 includes bidirectional current regulators 72A-72Q. Each of bidirectional current regulators 72A-72Q includes a corresponding one of regulated current sources 74A-74Q that delivers regulated stimulation current to the corresponding electrode and a corresponding one of regulated current sinks 76A-76Q that receives regulated stimulation current from the corresponding electrode.

For electrodes 48 designated as active electrodes in an electrode combination, stimulation control module 64 activates a respective current source 74 or current sink 76 depending on whether the electrode is a cathode or anode. Note that the block diagram illustrated in FIG. 6 is intended as a conceptual diagram that shows how stimulation generator 60 can be configured to control the operation of electrodes 48 in different modes, i.e., a regulated source mode, a regulated sink mode, or an off mode (in which both the source and sink may be disabled or disconnected). In other examples, stimulation generator 60 may further include switches to selectively couple some of electrodes 48 to $V_{HIGH}$ or $V_{LOW}$ via unregulated current paths for unregulated modes of operation In the example of FIG. 6, current sources 74 may be coupled at one end to the high supply voltage, $V_{HIGH}$, which may correspond to a high reference voltage level of voltage supply 62, and to a corresponding one of electrodes 48 at the other end. Current sinks 76 may be coupled at one end to the low supply voltage, $V_{LOW}$, which may correspond to low reference voltage level voltage supply 62, and to a corresponding one of electrodes 48 at the other end. High voltage ($V_{HIGH}$) and low reference voltage ($V_{LOW}$) represent high and low voltage levels of reference voltage 64 (FIG. 5) and may be supplied by power source 54 (FIG. 3). High voltage $V_{HIGH}$ and low voltage $V_{LOW}$ may be positive and negative voltages, respectively. In other examples, high voltage $V_{HIGH}$ may be a positive voltage and low voltage $V_{LOW}$ may be a ground voltage or other reference voltage.

Stimulation control module 64 controls the operation of regulated current sources 74A-74Q and regulated current sinks 76A-76Q to configure electrodes 48A-48Q as either inactive (i.e., off), regulated anodes, or regulated cathodes. For example, stimulation control module 64 may generate control signals to individually control regulated current sources 74A-74Q to deliver specified amounts of regulated current to electrodes 48A-48Q, respectively, and thereby configure such electrodes as regulated anodes. Similarly, stimulation control module 64 may generate control signals to individually control regulated current sinks 76A-76Q to receive specified amounts of regulated currents from electrodes 48A-48Q, respectively, and thereby configure such electrodes as regulated cathodes. For example, stimulation control module 64 may enable the current sources or sinks and also specify control voltages or control currents to be applied to the sources or sinks to control the amount of current that is sourced or sunk via the respective electrodes 48A-48Q. Processor 50 may control stimulation generator 60 to deliver stimulation according to a selected one or more of a plurality of programs or program groups stored in memory 52 such that stimulation current pulses are delivered with desired current levels, pulse rates, and pulse widths.

In an example, each current regulator, in the form of either regulated current source 74 or regulated current sink 76, may be implemented as a plurality of regulated current sources and sinks, respectively. The sources operate in parallel to produce a combined, programmable current source level sufficient for a desired stimulation therapy. Similarly, the sinks may operate in parallel with one another to provide a combined current sink level. A regulated current source 74, for example, may be implemented by several parallel regulated current source branches (×N) having identical or similar structures. Similarly, a regulated current sink may be implemented by several parallel regulated current sink branches (x N) having identical or similar structures.

Each individual current source or sink branch may be configured to provide a fixed amount of source or sink current, respectively. In this manner, each current source or sink branch sources or sinks, respectively, a fraction of a total amount of current that can sourced or sunk by a given current source 74 or current sink 76. A desired current source level for a given electrode 48 may be selected by selectively activating a corresponding number of the N parallel current source branches associated with a current source. Similarly, a desired current sink level for a given electrode 48 may be selected by selectively activating a corresponding number of the N parallel current sink branches associated with a current sink. In this manner, by activating a selected fraction of the parallel current sources or current sinks, a controlled, programmable amount of current may be sourced or sunk via a selected electrode 48.

As an example, each current regulator, e.g., regulated source 74A-74Q or regulated sink 76A-76Q, may be implemented by N parallel current regulator branches. As an example, N may be equal to 64 in some implementations. In this type of implementation, stimulation control module 64 may specify a reference source current and a reference sink current, e.g., based on program data specified automatically or by a user via an external programmer. For each electrode, stimulation control module 64 may further specify a percentage of the reference source current or reference sink current to be delivered via an electrode, e.g., based on program data. For example, stimulation control module 64 may specify that lead electrode 48, configured as an anode, should source 60% of the current to be delivered while lead electrodes 48B and 48C, also configured as anodes, substantially simultaneously source 15% and 25%, respectively, of the current to be delivered. Stimulation control module 64 may also specify that lead electrode 48D, configured as a cathode, should sink 100% of the current.

A control signal may be applied to each parallel current regulator branch such that the current levels produced by all N branches will add up to approximately the reference current level. Based on the percentage, which may be referred to as a gain ratio, stimulation control module 64 may selectively activate or deactivate a number of parallel current regulator branches for a given electrode sufficient to produce the specified percentage of the reference current. In this manner, stimulation control module 64 selectively scales up or scales down the number of active, parallel current regulator branches used by a given source 74 or sink 76. If the reference current is 20 milliamps (mA), for example, the control signal may be selected such that activation of all N parallel current regulator branches would produce 20 mA of source current or sink current, as applicable, for application via an electrode. In this case, the control signal may be selected such that each of the N current regulator branches produces $1/N^{th}$ of the reference current.

If the percentage to be delivered by a given electrode, e.g., electrode 48A, is 50 percent, then stimulation control module 64 activates 50 percent of the N parallel current regulator branches or, conversely, deactivates 50 percent of the N parallel current regulator branches. In either case, N/2 parallel current regulator branches are activated, producing a combined current of 50%×20 mA=10 mA to be sourced by electrode 48A in this example. Hence, when activated, each current regulator may source or sink a finite amount of current, determined as a function of the control signal, such that the fractional currents flowing in the parallel regulator branches can be summed to produce an overall regulated current. If the reference current is changed, the applicable control signal applied to each current regulator branch is changed.

By specifying percentages of source current and sink current for respective electrodes, stimulation control module 64 can control current sources and sinks 74 and 76 to precisely and selectively control the current level sourced by electrodes 48. In addition, the current levels sunk by particular electrodes 48 may also be precisely and selectively control. Further, stimulation control module 64 can support effective shaping of stimulation current to create different electrical stimulation fields or patterns useful in electrical stimulation therapy.

When turned "ON," each parallel current source or sink branch may produce a known amount of current, defined by the reference current and a corresponding control signal, as described above. In this manner, a source branch or sink branch may be considered either ON or OFF, and deliver the same fractional amount of current as other sources or sinks whenever it is ON. Alternatively, in some examples, each parallel current source or sink could be configured to provide different fractional amounts of current, or deliver variable amounts of current according to a bias or control signal. Although it is understood that each given source 74 or sink 76 may include multiple, parallel source branches or sink branches, this disclosure will generally refer to each of sources 74 and sinks 76 on a singular basis for ease of illustration.

Although current levels may be controlled by controlling a number of active current regulator branches as described above, in other examples, current may be controlled alternatively or additionally by directly controlling a current regulator in order to select a variable level of regulated current delivered via the current regulator. Hence, current levels may be controlled by selectively activating parallel current regulator branches with current levels that are set, based on a control signal, to sum to a desired current level, or by directly adjusting the level of current sourced or sunk by a given current regulator.

Although the use of parallel current regulator branches is described for purposes of illustration, either approach could be used. More particularly, in accordance with this disclosure, either approach may be used to control not only the current level sourced or sunk via a current regulator for a given stimulation current pulse, but also to vary the current level during the delivery of a stimulation current pulse. For example, as described in this disclosure, either approach may be used to control the pulse current level to decrease during the pulse width such that a sum of the pulse voltage level and a headroom voltage level of the current regulator does not exceed the supply voltage level, thereby maintaining substantial regulation of the current level.

The current pulse may be formed to have a slope or shape that is selected based on a decrease of the supply voltage level for the regulated output a during the delivery of the pulse and an increase in a load voltage for the load to which the pulse is delivered. The decrease in the supply voltage level and increase in the load voltage may be calculated based on measured or known values such as supply capacitance, load capacitance, pulse width, pulse current level, initial supply voltage, initial pulse voltage, the required headroom voltage between the pulse voltage and the supply voltage, and the like. This simulated decay of the current pulse level may prevent the sum of the pulse voltage level and the headroom voltage level from exceeding the supply voltage level, thereby preventing the pulse current level from falling out of regulation. In some cases, with this technique, it may be possible to use a smaller supply voltage to deliver a stimulation current pulse with a desired average current level.

Figure 7A:
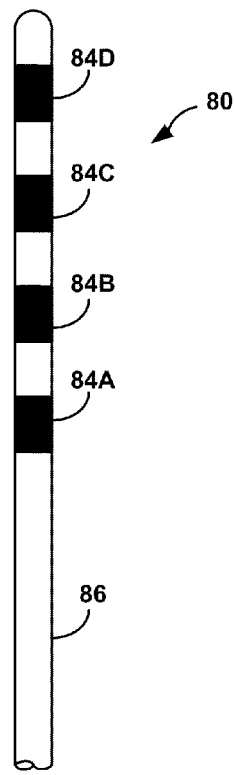
FIGS. 7A and 7B are conceptual diagrams illustrating example leads and electrode configurations that may be used for delivering electrical stimulation therapy as described in this disclosure.
Figure 7B:
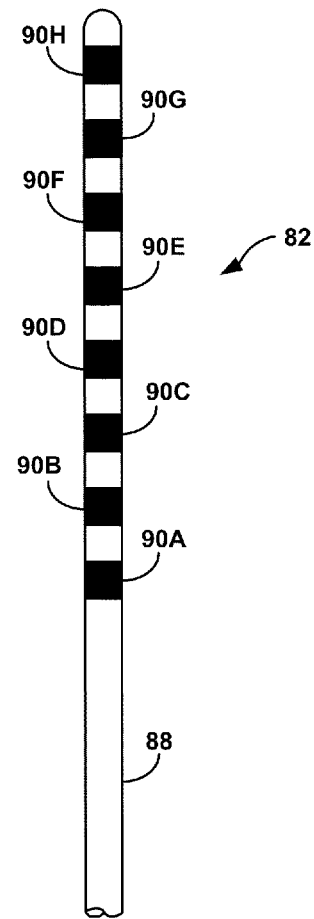

FIGS. 7A and 7B are conceptual diagrams illustrating two different implantable stimulation leads. Leads 80 and 82 are examples of leads 12A, 12B and 32A, 32B shown in FIGS. 1 and 2. As shown in FIG. 7A, lead 80 includes four electrodes 84A-84D mounted at various lengths of lead body 86. Lead 82 includes lead body 88, carrying eight electrodes 90A-90H. Electrodes 84A-84D may be equally spaced along the axial length of lead body 86 at different axial positions. Although not depicted, in some examples, each electrode 84, 90 may formed by two or more electrode segments located at different angular positions around the circumference of lead body 86 or 88, forming segmented electrodes.

Electrodes of one circumferential location may be lined up on an axis parallel to the longitudinal axis of lead 80 or 82. Alternatively, different electrodes may be staggered around the circumference of lead body 86. In addition, lead 80 or 82 may include asymmetrical electrode locations around the circumference of each lead or electrodes of the same level that have different sizes. These electrodes may include semi-circular electrodes that may or may not be circumferentially aligned. Lead body 86 or 88 may include a radio-opaque stripe (not shown) along the outside of the lead body. Each electrode may be substantially rectangular in shape. Alternatively, the individual electrodes may have alternative shapes, e.g., circular, oval, triangular, or the like.

Figure 8:
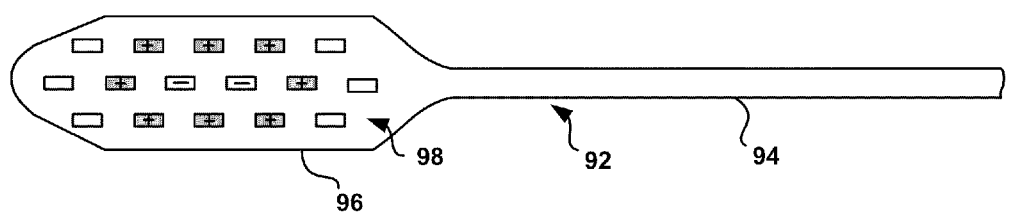
FIG. 8 is a conceptual diagram illustrating an example paddle lead that may be used for delivering electrical stimulation therapy as described in this disclosure.

FIG. 8 is a conceptual diagram illustrating an example paddle lead 92 that additionally or alternatively may be used for delivering electrical stimulation in accordance with the techniques in this disclosure. In the example of FIG. 8, lead 92 includes a lead body 94 and a lead paddle section 96 carrying an array of electrodes 98 arranged in three rows having five, six and five electrodes, respectively. As an illustration of one possible electrode configuration, electrodes 98 indicated by plus (+) signs are anodes, electrodes indicated by minus (−) signs are cathodes, and electrodes without signs are inactive electrodes. Paddle lead 92 may be configured to include lesser or greater numbers of electrodes. In some implementations, paddle lead 92 may be similar to the Specify™ 5-6-5 paddle lead commercially available from Medtronic, Inc. of Minneapolis, Minn.

Figure 9:
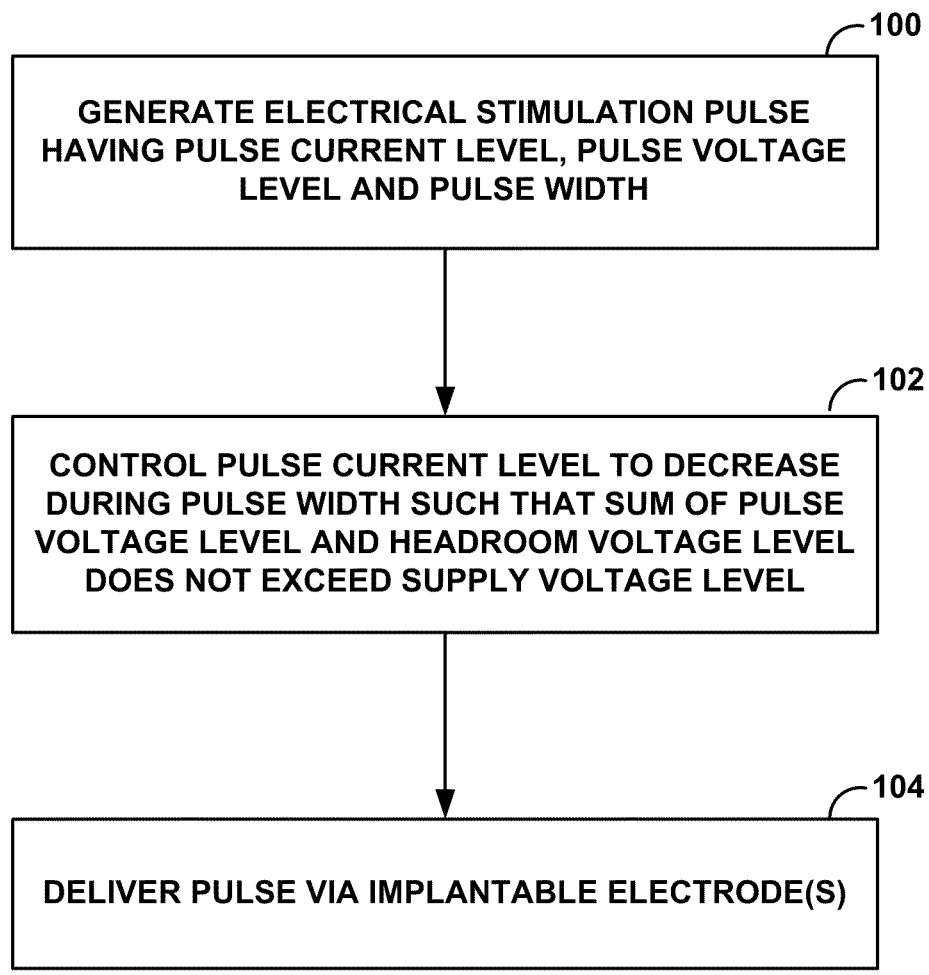
FIG. 9 is a flow diagram illustrating delivery of electrical stimulation as described in this disclosure.

FIG. 9 is a flow diagram illustrating delivery of electrical stimulation as described in this disclosure. As shown in FIG. 9, an electrical stimulation generator, such as generator 60 of FIG. 3 or 5, generates an electrical stimulation pulse having a pulse current level, a pulse voltage level and a pulse width (100). The pulse current level may be regulated, and thereby controlled to deliver a desired pulse current level. The pulse voltage level may vary over the course of the delivery of the stimulation pulse. In particular, the pulse voltage level ordinarily may increase over the course of the delivery of the stimulation pulse to biological tissue as a voltage on a load capacitance associated with the conductive path from the regulator to the electrode and voltage on a load capacitance associated with the tissue-electrode interface increases. As discussed above, typically, as the stimulation current pulse is delivered, there is a decrease in the level of the supply voltage provided by the voltage supply and used by the current regulator to deliver the pulse, due to partial discharging of one or more capacitors forming a supply capacitance that provides the supply voltage.

If the sum of the pulse voltage level and the headroom voltage level exceeds the supply voltage provided to the current regulator, the stimulation current level may not be properly regulated. In particular, as the pulse is delivered, the specified current level may fall out of regulation toward the end of the pulse width as the supply voltage drops and the pulse voltage rises. For a cathodic (sink) pulse or an anodic (source) pulse, the stimulation pulse voltage level can be considered to exceed the supply voltage level if the absolute value of the stimulation pulse voltage level plus the headroom voltage is greater than the absolute value of the supply voltage level. In accordance with an aspect of this disclosure, to maintain regulation of the stimulation pulse current level, stimulator generator 60 may control the pulse current level to decrease during the pulse width such that a sum of the pulse voltage level and the headroom voltage level of the current regulator does not exceed the supply voltage level (102). Stimulation generator 60 delivers the pulse to a biological tissue load, e.g., associated with a patient, via one or more implantable electrodes (104). Delivery of the pulse may refer to delivery of a sink pulse or a source pulse, in which cases current may be cathodic or anodic, respectively.

Because the pulse voltage level is a function of the pulse current level, a decrease in the pulse current level may cause a proportional decrease in the pulse voltage level. In other words, the amount of pulse current voltage necessary to deliver the pulse current level may be decreased. Hence, if the pulse voltage level increases during delivery of the pulse due to an increase in the load voltage, with a decreasing pulse current level, the amount of the increase in the pulse voltage level may be less than if a constant pulse current level was delivered during the pulse width. During the delivery of a stimulation pulse, the supply voltage may decrease, due to discharging of one or more supply capacitors, with a known, calculated or measured discharge profile, which may be linear or nonlinear, and which may vary as a function of the initial supply voltage level, the supply capacitance, load capacitance, regulator overhead voltage, and the regulated current level delivered by stimulation generator 60. Similarly, the load voltage, due to charging of the load capacitance, may increase during the pulse width according to a known, calculated or measured charge profile.

Stimulation generator 60 may form the current pulse to have a decreasing profile that prevents the sum of the headroom voltage and the pulse voltage level from exceeding the supply voltage level. The profile may be, as examples, a linear slope or a nonlinear curve. In some examples, if there was no load capacitance, the pulse current level could approximately match a decay slope or profile of the supply voltage level for the regulated output as the supply voltage level decreases. In this case, the slope of the pulse could be considered optimum if it matched the slope of the supply voltage. However, a load capacitance may be presented by series capacitors on the electrical path from the current regulator output to the electrode as well as a capacitance presented by the electrode-tissue interface. These capacitances may be combined to form a load capacitance. The load capacitance may build up charge during the delivery of the pulse.

As an illustration, in one implementation, the voltage supply could have a capacitance of 22 microfarads (µF) and the load capacitance could be 5 µF. In this case, the voltage on the load capacitance would increase more quickly than the voltage on the supply capacitance would decrease. In another implementation that could be used to decrease IMD size, the voltage supply could be configured to only have 1 µF in capacitance, which would then decrease in voltage faster than the voltage increase on the series electrode capacitors in the load capacitance. In both of these examples, the capacitances of both the load and the voltage supply can be utilized to find a desirable curve-fit for the shape or profile of the controlled current output of the current regulator. In particular, the regulated current may have a decreasing current level profile that is selected as a function of the supply capacitance and load capacitance.

The decreasing profile may be defined, for example, by a linear slope, a nonlinear curve, or a piecewise series of sub-pulses with progressively decreasing current levels, or other shapes. The current profile may be presented, for example, by a continuous, decaying pulse waveform, or a combination of two or more sub-pulses with progressively decreasing current levels in a split pulse that provide a piecewise decrease in current level. If one capacitance is much larger than the other (e.g., supply capacitance much greater than load capacitance or load capacitance much greater than supply capacitance), it may be possible to ignore the larger capacitance in the determination of the appropriate pulse current level profile for simplicity. In each case, the pulse current level may, in effect, undergo a simulated decay that can be determined as a function of a decay in the supply voltage level and/or an increase in the load voltage level over the pulse width.

Figure 10:
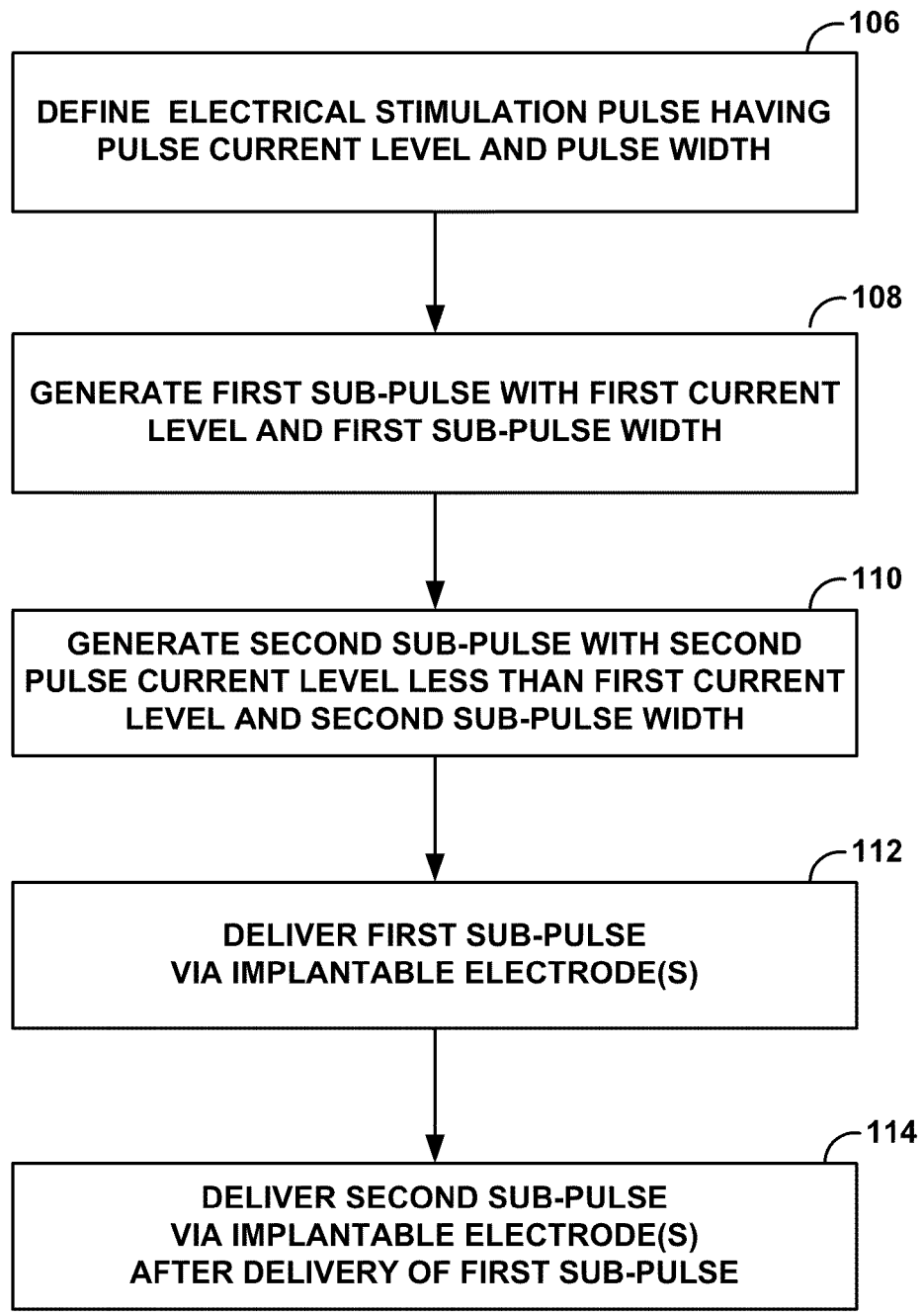
FIG. 10 is a flow diagram illustrating delivery of electrical stimulation as described in this disclosure.

FIG. 10 is a flow diagram illustrating delivery of electrical stimulation as described in this disclosure. In particular, FIG. 10 illustrates an example technique for controlling pulse current level to decrease during the pulse width such that the pulse voltage level does not exceed the supply voltage level. As shown in FIG. 10, stimulation generator may define an electrical stimulation pulse having a pulse current level and a pulse width (106). The pulse current level for a given pulse may be specified based on stimulation pulse parameters associated with a stimulation program. The pulse parameters may be specified for stimulation generator 60 by processor 50 based on program data stored in memory 52 (FIG. 3). The pulse parameters may include, in addition to pulse current level and pulse width, pulse rate, and electrode configuration. The electrode configuration may specify electrodes and polarities for delivery of the stimulation pulse.

Although generation of a single pulse is described with reference to FIG. 10 for ease of illustration, it will be understood that stimulation generator 60 may deliver a series of such pulses at specified intervals or according to a desired pulse rate, i.e., pulse frequency, and possibly according to a desired duty rate. Such pulses may be delivered in a continuous pulse train at a desired pulse rate or in bursts of pulses. Stimulation generator 60 may control the pulse current level of all pulses, as described in this disclosure, to prevent the pulse voltage level from exceeding the supply voltage level. Alternatively, stimulation generator 60 may control the pulse current level in this manner for selected pulses, such that not every pulse is controlled to prevent the pulse voltage level from exceeding the supply voltage level. Typically, however, it may be desirable to control all stimulation pulses to prevent the pulse voltage level from exceeding the supply voltage level.

In the example of FIG. 10, to control the pulse current level to decrease during the pulse width, stimulation generator 60 generates a first sub-pulse with a first current level and first sub-pulse width (108), and generates a second sub-pulse with a second current level less than the first current level and a second sub-pulse width (110). The second sub-pulse follows the first sub-pulse in time. The first and second sub-pulses may have sub-pulse widths that fit within the pulse width of the defined pulse (106) from which they are sub-divided, i.e., split. Stimulation generator 60 delivers the first sub-pulse via one or more implantable electrodes (112) and delivers the second sub-pulse via one or more implantable electrodes after delivery of the first sub-pulse (114). Hence, the second sub-pulse follows the first sub-pulse in time, and has a second current level that is less than the first current level of the first sub-pulse. The first and second current levels may be fixed during the duration of the first and second sub-pulse widths, respectively. Alternatively, in some examples, the first and second current levels may vary, e.g., decrease from an initial value to a lower value, during the first and second sub-pulse widths, respectively. In either case, in some examples, the average of the pulse current level during the first and second sub-pulses may be selected such that the sum of the pulse voltage level and the headroom voltage level does not exceed the supply voltage level.

The first and second sub-pulse widths may be selected such that the sum of the first and second sub-pulse widths is equivalent or substantially equivalent to the pulse width of the defined pulse, i.e., the pulse defined in (106). In this manner, the first and second sub-pulses may fit within the pulse width of pulse for which they are generated. The first and second sub-pulse widths may be equal to one another or different from one another, i.e., nonequal. In effect, the sub-pulses are delivered, one after the other, to approximate the current level and pulse width of the defined electrical stimulation pulse. Although two sub-pulses are discussed with respect to the example of FIG. 10, in other examples, the defined split pulse may be delivered using more than two sub-pulses, such as three, four or more sub-pulses, each having respective current levels and sub-pulse widths. In each case, the sub-pulse widths may be the same or different. The sub-pulse current levels ordinarily may be different from one another, and may decrease such that earlier sub-pulses delivered for a given pulse tend to have higher current levels than later sub-pulses delivered for the given pulse.

The first and second current levels may be selected such that the pulse current level during the delivery of the first and second sub-pulses (or more than two sub-pulses) decreases according to a decrease in the supply voltage level (due to discharge of the supply capacitance) and/or an increase in pulse voltage level (due to charging of the load capacitance) during the pulse width. For example, the pulse current level during the delivery of the first and second sub-pulses may have a current level that is selected to decrease over time to prevent the sum of pulse voltage level and the headroom voltage level from exceeding the supply voltage level during the pulse width, given the decrease in the supply voltage level and the increase in the pulse voltage level over the course of the pulse width. In some implementations, an average pulse current level during the first and second sub-pulses may be calculated based on the discharge profile of the supply capacitance and the charge profile of the load capacitance.

As the pulse current level decreases during the pulse width, the pulse voltage level may increase during the pulse width and the supply voltage level may decrease during the pulse width. The decrease in the supply voltage level may be impacted by an increase in required voltage due to the capacitance of the load. However, the decrease in pulse current level may be selected to prevent the increasing pulse voltage level from exceeding the decreasing supply voltage level. As less pulse current is delivered, either by decreasing the current level of a single pulse, or by delivering sub-pulses with progressively smaller current levels, less pulse voltage is needed to deliver that current for a given load impedance. In this manner, the sum of the pulse voltage level and the headroom voltage can remain below the supply voltage level so that regulation of the pulse current level can be maintained during the pulse width.

Although the pulse current level decreases during the pulse width, the amount of current delivered to the patient may be approximately equal to the amount of current that would be delivered with a constant current level. In one example, for a pulse formed by first and second sub-pulses, the first sub-pulse may have a current level that is greater than the constant current level that otherwise would have been used to deliver the pulse, and the second sub-pulse may have a current level that is less than the constant current level that otherwise would have been used to deliver the pulse. In some cases, the average current level of the two sub-pulses may be substantially equal to the constant current level specified for the pulse.

Figure 11A:
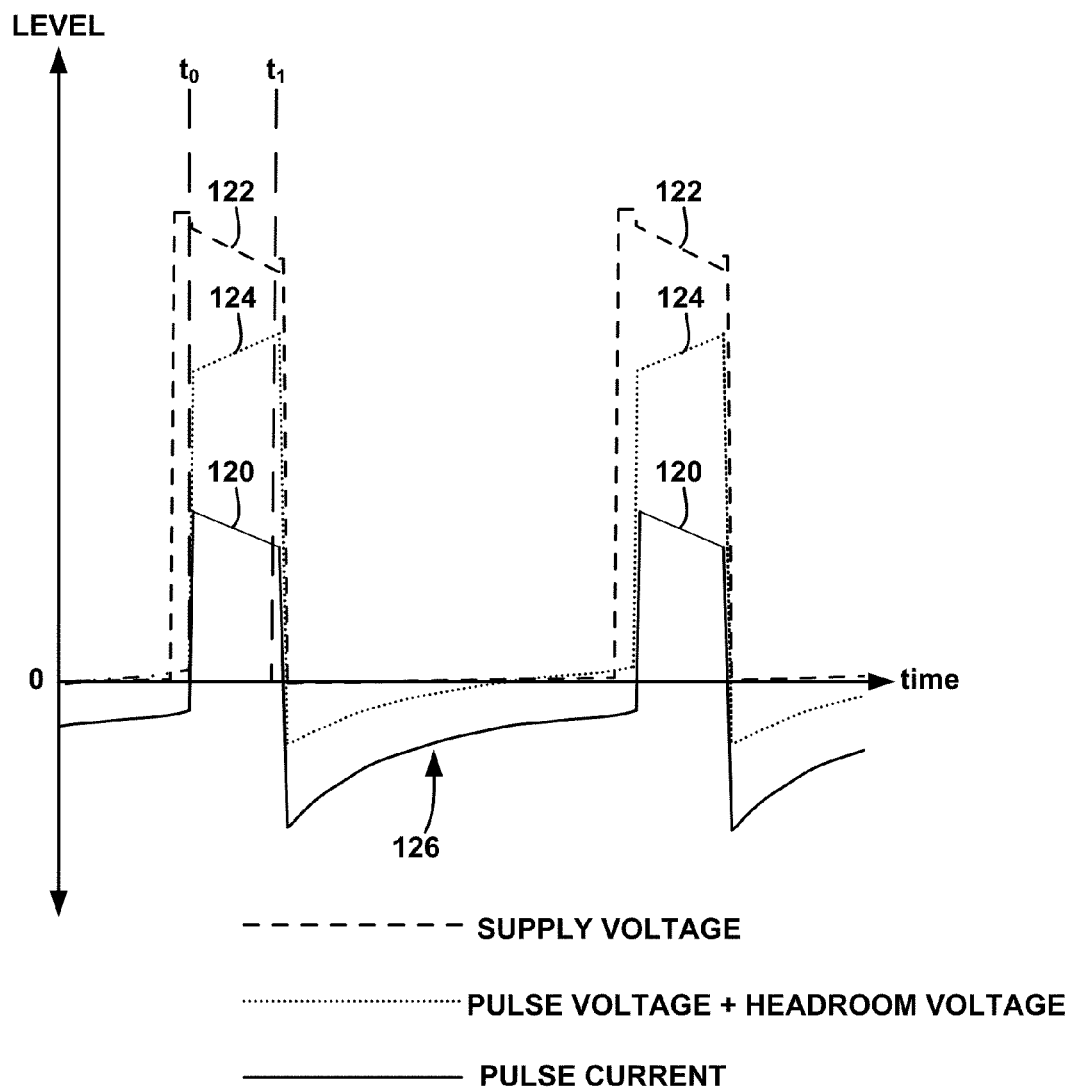
FIGS. 11A and 11B are graphs illustrating example stimulation pulses delivered according to examples of this disclosure.
Figure 11B:
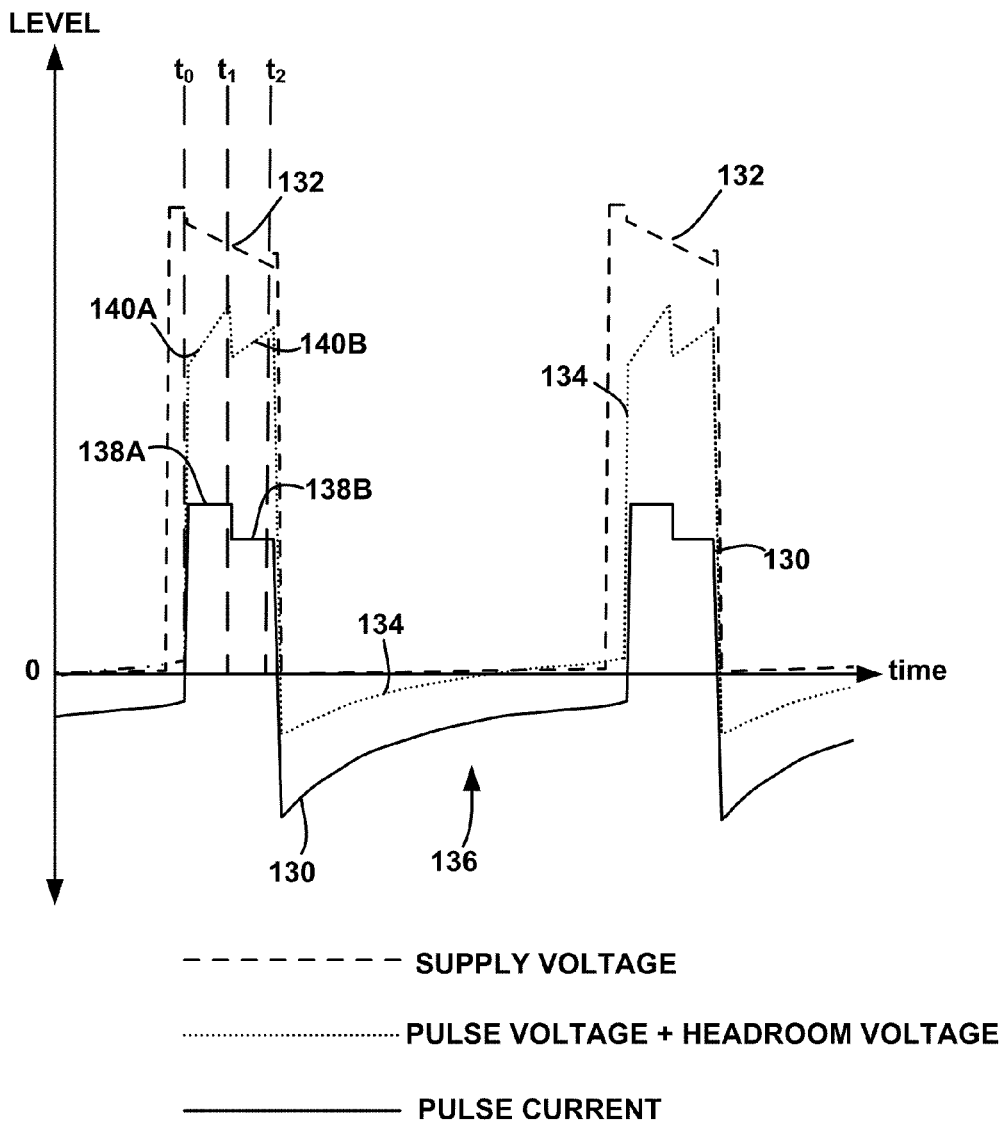

FIGS. 11A and 11B are graphs illustrating example stimulation pulses delivered according to examples of this disclosure. In FIGS. 11A and 11B, the horizontal axis represents time and the vertical axis represents current or voltage level. As shown in FIGS. 11A and 11B, the pulse current level may be controlled by stimulation generator 60 to decrease during the pulse width such that the sum of the pulse voltage level and the headroom voltage does not exceed a supply voltage level. In particular, the pulse current level can be controlled to decrease according to a decrease in the supply voltage level and an increase in voltage from the load capacitance during the pulse width.

As an illustration, in some examples, the pulse current level may be controlled to have a decay profile, such as a linear slope, that is determined based on a decay, characterized by a decreasing slope, of the supply voltage level during the pulse width. In addition, the pulse current level may be controlled to have a decay profile that is determined based on an increase in load voltage due to charging of a load capacitance during the pulse width. In some cases, the pulse may comprise first and second sub-pulses. The second sub-pulse follows the first sub-pulse in time and has a pulse current level that is less than the pulse current level of the first sub-pulse. In other cases, the pulse may comprise more than two sub-pulses. The pulse current levels of the sub-pulses may be selected to have an average current level that is determined based on a decrease in the supply voltage level and an increase in the load voltage level.

For a given pulse, with a programmed current level, stimulation generator 60 may generate a decreasing pulse current level profile for a single pulse, or a set of sub-pulses with specified current levels to deliver the pulse. The profile and/or sub-pulse levels may correspond to a desired average current specified by the programmed current level, and may be determined using calculations by processor 50 of stimulator 34 (or stimulator 4), or processor 53 of programmer 40 (or programmer 42, 20 or 22), or based on pre-stored mappings (e.g., pulse current level to sub-pulse current levels) in memory 52 of stimulator 34 (or stimulator 4), or in memory 55 of programmer 40 (or programmer 42, 20 or 22).

In each case, the calculations or mappings may be generated based on calculations, measurement or knowledge of the actual discharge profile of the voltage supply and the increase profile of the load voltage, based on supply capacitance, load capacitance, load impedance, headroom voltage, and other characteristics such as pulse current level and pulse width. Knowledge of the voltage supply discharge profile and load voltage charge profile may be obtained in some examples, based on measurements taken, e.g., in a laboratory or in the factory, or by stimulator 4 or 34, for different voltage levels, current levels and pulse widths, to characterize the profiles.

In some examples, profile or sub-pulse determinations may be made within the IMD (e.g., stimulator 4 or 34) based on a current level specified by a program provided by programmer 20, 22, 40 or 42, or possibly made within an external programmer such as one of programmers 20, 22, 40 or 42 and conveyed to the IMD via telemetry, e.g., as sub-pulse current levels. Alternatively, as discussed above, such determinations may be pre-computed and stored as a mapping in memory of either stimulator 4 or 34, or any of programmers 20, 22, 40 and 42.

In the example of FIG. 11A, the graph illustrates delivery of two successive stimulation current pulses, with a pulse current level represented by trace 120. The supply voltage level is represented by trace 122. The sum of the pulse voltage level and an applicable headroom voltage level is represented by trace 124. The headroom voltage level may be specified for a particular current regulator, based on the amount of voltage required by circuit components of the current regulator. In some examples, the headroom voltage level may include this voltage required by the circuit components pulse a small margin voltage.

As shown in FIG. 11A, over a pulse width extending from time t0 to time t1, the pulse current level 120 decreases from an initial current level at time t0 to a reduced current level at time t1. Hence, the pulse current level decreases over the duration of the pulse width as described in this disclosure. After time t1, the pulse current level 120 and the sum of the pulse voltage level and headroom voltage 124 drop and then recover during a passive recharge cycle, generally indicated by reference number 126. In some cases, an active recharge cycle may be applied instead of, or in addition to, a passive recharge cycle. During the delivery of each pulse, from t0 to t1, the level of a supply voltage 122 for the current regulator that delivers the pulse decreases, i.e., due to discharging of one or more capacitors associated with the voltage supply.

As the supply voltage level 122 decreases over the pulse width, the sum of the pulse voltage level and headroom voltage 124 increases. As shown in FIG. 11A, however, the decrease in the pulse current level 120, in accordance with various aspects of this disclosure, is effective in maintaining the sum of the pulse voltage level and headroom voltage 124 below the supply voltage level 122. If the pulse current level 120 was maintained at a constant level during the pulse width, it is possible that the sum of the pulse voltage level and headroom voltage 124 could exceed the supply voltage level 122, penetrating the headroom of the current regulator, and undermining effective regulation of the pulse current level.

By reducing the pulse current level 120 over time, the sum of the pulse voltage level and headroom voltage 124 does not rise as high as it otherwise could rise. Yet, the pulse current level 120, and the slope of the decrease, can be selected such that the pulse still delivers a desired average current level over the pulse width. As shown in the example of FIG. 11A, the average slope of the decrease in the pulse current level 120 could be selected to approximate the average slope of a decrease in the supply voltage level 122 if the voltage on the load capacitance was not taken into account. With the load voltage, however, the slope of pulse current level 120 may be different from the slope of supply voltage level 122. In some cases, the slope of the decrease in pulse current level 120 may be constant and linear, or may vary in a nonlinear manner.

The pulse current level 120 may be selectively controlled by stimulation generator 60 to output different current levels at different times during the duration of the pulse width. For example, stimulation generator 60 may control activation of a number of parallel current regulator branches or directly control a current delivered by a given current regulator in order to provide a pulse shape that decreases in current level from a start of the pulse width to an end of the pulse width, as shown in FIG. 11A. Hence, the pulse current level may be continuously controlled or controlled over a series of time slots or sub-pulses, as will be described in further detail with reference to the example of FIG. 11B. In either case, the current level may decrease over time to prevent the pulse voltage level from exceeding the supply voltage level.

With the decrease in the pulse current level 120, a higher average current can be delivered by stimulation generator 60 in a controlled manner without the need to increase the supply voltage level in order to prevent the pulse voltage level from exceeding the supply voltage level. By avoiding an increase in supply voltage level, the techniques described in this disclosure may, in some cases, permit longer battery life or longer time between recharges in the case of a rechargeable battery, as well as minimal or no effect on therapeutic outcome. In some cases, the voltage supply for the current regulator may use downsized capacitor values to generate the required pulse voltage, allowing the use of smaller electrical hybrid circuitry, smaller devices, or larger batteries.

In the example of FIG. 11B, the graph illustrates delivery of two successive stimulation current pulses, where each pulse is split, i.e., sub-divided, into first and second sub-pulses with different current levels. As an example, the average pulse current level during the first and second sub-pulses may be selected and controlled by stimulation generator 60 such that the sum of the pulse voltage level and the headroom voltage for the regulator does not exceed the supply voltage level for the regulator during the pulse width. In FIG. 11B, pulse current level is represented by trace 130, supply voltage level is represented by trace 132, and the sum of the pulse voltage level and the headroom voltage is represented by trace 134. A passive recharge cycle is generally indicated by reference numeral 136, although an active recharge could be used in some examples. Each pulse in the example of FIG. 11B, extending from time t0 to time t2, is divided into a first sub-pulse 138A and a second sub-pulse 138B. In other examples, multiple sub-pulses may be delivered for each pulse.

The second sub-pulse 138B follows the first sub-pulse 138 in time and has a pulse current level that is less than the pulse current level of the first sub-pulse. In this sense, the pulse delivered between time t0 and time t1 may be split into two portions: a higher current portion provided by sub-pulse 138A and a lower current portion provided by sub-pulse 138B. First sub-pulse 138A is delivered from time t0 to time t1, and second sub-pulse 138B is delivered from time t1 to time t2. Again, in other cases, the pulse may comprise more than two sub-pulses, such as high, medium and low portions, or a greater number of sub-pulses providing even greater granularity in current level. In general, the proportion of the higher current level or levels to the lower current level or levels may be determined based on the decrease of the supply voltage level 132 and an increase in a load voltage. For example, the pulse current levels of the sub-pulses 138A, 138B may be selected to produce an average current level that approximates a slope of the supply voltage level 134 during the pulse width from time t0 to time t1, as described above, if the contributions of the load capacitance are ignored. Alternatively, the average current level may be determined based on the negative slope on the supply voltage level and the positive slope of the voltage on the load capacitance during the pulse width.

As further shown in FIG. 11B, the different current levels of the first and second sub-pulses 138A, 138B may have an effect on the voltage levels of the sub-pulses. In particular, sub-pulse 138A may have a current level that produces a sum of the pulse voltage level and headroom voltage 140A from approximately time t0 to t1, and sub-pulse 138B may have a current level that produces a sum of pulse voltage level and headroom voltage 140B from approximately time t1 to t2. In general, as the load voltage increases, due to charging of the load capacitance, the pulse voltage level that is needed to maintain a desired, regulated pulse current level also needs to increase. As supply voltage level 132 drops and the required pulse voltage needs increase (as a result of an increase in the voltage on the load capacitance) between time t0 and t2, the delivery of the reduced current level for sub-pulse 138B limits the increase of the sum of the pulse voltage level and headroom voltage 140B so that the sum of the pulse voltage level and the headroom voltage, even though it increases, remains below supply voltage level 132, thereby preserving voltage overhead in the current regulator to prevent the pulse current level from going out of regulation.

In some cases, this approach may permit a smaller supply voltage to be used to deliver a stimulation current pulse with a desired average current level. As an illustration, assume that a voltage supply ordinarily would require an initial voltage level of 5 volts to support delivery of a given stimulation current pulse because the voltage supply would decay to 4.7 volts while the pulse voltage would rise to 4.5 volts, assuming a requirement for 0.2 volts of headroom voltage in the current regulator. If the stimulation current level is decreased over the pulse width while producing the same average current, but the resulting pulse voltage level rises to only 4.3 volts, then the voltage supply could have an initial value of only 4.8 volts. The reduced initial voltage requirement for the voltage supply in this scenario could permit the voltage supply to be constructed with reduced size capacitor module.

In the examples of FIGS. 11A and 11B, for purposes of illustration, the graphs illustrate anodic current pulses in which current levels and voltage levels are positive. However, the techniques described in this disclosure may be applied for both anodic and cathodic current pulses. In each case, the magnitude of the pulse current level may be decreased to prevent the magnitude of the pulse voltage level plus the headroom voltage from exceeding the magnitude of the supply voltage level during the course of the pulse width. In other words, the pulse current level is controlled so that the absolute value of the pulse voltage level plus the headroom voltage does not exceed the absolute value of the supply voltage level.

As discussed above, multiple sub-pulses may be used to deliver a pulse waveform having a current level that decreases over the course of its pulse width. In some cases, delivery of two sub-pulses for each pulses may be effective and even desirable. If stimulation generator 60 includes a redundant current regulator for each electrode, for example, one current regulator could be used to deliver a first sub-pulse and a second regulator could be used to deliver a second sub-pulse that follows the first sub-pulse in time and has a current level that is less than a current level of the first sub-pulse. The current regulators may be triggered by control signals at time t0 and t1, respectively, or the second current regulator may be triggered based on a delay running from the time the first current regulator is activated.

Splitting a stimulation current pulse into sub-pulses may be performed in a variety of ways. As described above, the sub-pulses may have different current levels and either equal or nonequal sub-pulse widths. The current level for each sub-pulse is substantially constant for the duration of the respective sub-pulse width. Set forth below is a discussion of an example process for determining current levels for two sub-pulses forming an overall pulse. Splitting a stimulation pulse into two sub-pulses with different stimulation current levels allows a pulse with the same total charge to be delivered while requiring less voltage on the supply capacitor module associated with the voltage supply, which may be formed by a capacitor stack with a selectable number of capacitors, but which will be referred to generally below as a supply capacitor for convenience. As an example, instead of delivering a 3 milliamp (mA) constant current pulse, a pulse may be subdivided into a first sub-pulse with a first sub-pulse width and a current level of 3.5 mA and a second sub-pulse with a second sub-pulse width equal to the first sub-pulse with and a current level of 2.5 mA, resulting in an average current of 3 mA, which is equal to the average current of the desired 3 mA constant current pulse.

In determining how to split a pulse between sub-pulses, and assigning sub-pulse current levels, it may be desirable to determine what constitutes an optimum split. The following discussion addresses this question in terms of selecting the first and second sub-pulse current levels that minimize the required supply voltage level necessary to deliver a given average current level. The discussion takes into account several different parameters including the supply voltage $V_{sc}$ on the voltage supply capacitor, the stimulation pulse voltage $V_{stim}$, the voltage on the load capacitance $V_{LC}$, and the current regulator headroom voltage requirement $V_H$. Values for some of these parameters may be measured. For example, the supply capacitance, load capacitance and charge and discharge profiles can be determined by measurement in a laboratory or factory, or measurement by a stimulator 4, 34. Headroom voltage refers to the minimum voltage difference between the supply voltage of the current regulator and the stimulation pulse voltage to ensure proper operation of the current regulator and, hence, reliable regulation of the pulse current level. The conclusion from the analysis presented below is that a 50/50 split in pulse width between two sub-pulses forming a pulse may be most desirable, although other split ratios may be used with less optimal but suitable results.

The voltage $V_{scend1}$ on the supply capacitor at the end of the first sub-pulse $Stim_1$ (i.e., after decay of the initial voltage $V_{sc}$) must be at least the sum of the first stimulation sub-pulse voltage $V_{stim1}$, the voltage on the load capacitance $V_{LC1}$ at the end of first sub-pulse $Stim_1$, and the headroom voltage $V_H$ such that:

$$V_{scend1} >= V_{stim1} + V_{LC1} + V_H$$

In the following equations, * designates the multiplication operation. The voltage $V_{scbeg1}$ on the supply capacitor at the beginning of the first sub-pulse $Stim_1$ should be at least equal to the supply voltage $V_{scend1}$ at the end of the first sub-pulse $Stim_1$ plus the charge that is used to deliver the first sub-pulse $Stim_1$ such that:

$$V_{scbeg1} >= V_{scend1} + (i_{stim1}*pw_1)/C_{sc} = V_{stim1} + V_{LC1} + V_H + (i_{stim1}*pw_1)/C_{sc}$$

where $i_{stim1}$ is the current level of the first sub-pulse, $pw_1$ is the pulse width of the first sub-pulse, and $C_{sc}$ is the capacitance of the supply capacitor for the voltage supply. The first sub-pulse $Stim_1$ may be generally defined as a square wave current pulse that goes from zero milliamps (or some other reference current level) to the desired sub-pulse current level of $i_{stim1}$. Although a square wave ordinarily may be used, other sub-pulse shapes for the first sub-pulse may be possible.

For the second sub-pulse $Stim_2$, the voltage on the voltage supply capacitor $V_{scend2}$ at the end of the second sub-pulse $Stim_2$ must be at least the sum of the second stimulation sub-pulse voltage $V_{stim2}$, the voltage developed on the load capacitance $V_{LC1}$ during the first sub-pulse $Stim_1$, the voltage developed on the load capacitance $V_{LC2}$ during the second sub-pulse $Stim_2$ and the headroom voltage $V_H$ such that:

$$V_{scend2} >= V_{stim2} + V_{LC1} + V_{LC2} + V_H$$

The voltage $V_{scbeg2}$ on the supply capacitor at the beginning of the second sub-pulse $Stim_2$ should be at least equal to the supply voltage $V_{scend2}$ at the end of the second sub-pulse $Stim_2$ plus the charge that is used to deliver the second sub-pulse $Stim_2$ such that:

$$V_{scbeg2} >= V_{scend2} + (i_{stim2}*pw_2)/C_{sc} = V_{stim2} + V_{LC1} + V_{LC2} + V_H + (i_{stim2}*pw_2)/C_{sc}$$

$$V_{scbeg2} = i_{stim2}{}^*R_{load} + (i_{stim1}{}^*pw_1)/C_{load} + (i_{stim2}{}^*pw_2)/C_{load} +$$
$$(i_{stim2}{}^*pw_2)/C_{sc} + V_H$$
$$= (i_{stim} - x)^*R_{load} + ((i_{stim} + x)^*pw_1)/C_{load} +$$
$$((i_{stim} - x)^*pw_2)/C_{load} + ((i_{stim} - x)^*pw_2)/C_{sc} + V_H$$
$$= i_{stim}{}^*R_{load}{}^*C_{load}/C_{load} - x^*R_{load}{}^*C_{load}/C_{load} + i_{stim}{}^*$$
$$pw_1/C_{load} + x^*pw_1/C_{load} + i_{stim}{}^*pw_2/C_{load} -$$
$$x^*pw_2/C_{load} + (Istim^*pw_2)/C_{sc} - (x^*pw_2)/C_{sc} + V_H$$
$$= (1/C_{load})^*(i_{stim}{}^*R_{load}{}^*C_{load} - x^*R_{load}{}^*C_{load} + i_{stim}{}^*pw_1 + x^*pw_1 + i_{stim}{}^*pw_2 - x^*pw_2) +$$
$$(Istim^*pw_2)/C_{sc} - (x^*pw_2)/C_{sc} + V_H$$

where $i_{stim2}$ is the current level of the second sub-pulse, $pw_2$ is the pulse width of the second sub-pulse, and $C_{sc}$ is the capacitance of the supply capacitor. The second sub-pulse $Stim_2$, like the first sub-pulse, may be generally defined as a square wave current pulse that goes from zero milliamps (or some other reference voltage) to the desired sub-pulse current level of $i_{stim2}$. Again, although a square wave ordinarily may be used, other sub-pulse shapes for the second sub-pulse may be possible.

The initial voltage $V_{sc}$ required on the supply capacitor to support proper regulation depends on the relationship between $V_{scend1}$ and $V_{scbeg2}$. If $V_{scend1}$ is greater than $V_{scbeg2}$, then $V_{sc}$ is determined by the first sub-pulse $Stim_1$, where:

$$\text{Required } V_{sc} = V_{scbeg1}.$$

Alternatively, if $V_{scbeg2}$ is greater than $V_{scend1}$, then $V_{sc}$ is determined by the second sub-pulse $Stim_2$, where:

$$\text{Required } V_{sc} = V_{scbeg2} + (i_{stim1}*pw_1)/C_{sc}.$$

The lowest required $V_{sc}$ occurs when $V_{scend1} = V_{scbeg2}$. Let x be the current that is added to $i_{stim1}$ and subtracted from $i_{stim2}$ and let $i_{stim}$ be the average current as follows:

$$i_{stim1} = i_{stim} + x$$

$$i_{stim2} = i_{stim} - x$$

Upon setting $V_{scend1} = V_{scbeg2}$, $i_{stim1}$ and $i_{stim2}$ are replaced with the above values, permitting the equations to be solved for x as represented by the following equations:

$$V_{scend1} = i_{stim1}{}^*R_{load} + (i_{stim1}{}^*pw_1)/C_{load} + V_H$$
$$= (i_{stim} + x)^*R_{load} + ((i_{stim} + x)^*pw_1)/C_{load} + V_H$$
$$= i_{stim}{}^*R_{load}{}^*C_{load}/C_{load} + x^*R_{load}{}^*C_{load}/C_{load} +$$
$$i_{stim}{}^*pw_1/C_{load} + x^*pw_1/C_{load} + V_H$$
$$= (1/C_{load})^*(i_{stim}{}^*R_{load}{}^*C_{load} + x^*pw_1 + i_{stim}{}^*pw_1 + x^*R_{load}{}^*C_{load})$$
$$+ V_H$$

$$V_{scend1} = V_{scbeg2}(1/C_{load})^*\begin{pmatrix} i_{stim}{}^*R_{load}{}^*C_{load} + x^*pw_1 + \\ i_{stim}{}^*pw_1 + x^*R_{load}{}^*C_{load} \end{pmatrix}$$
$$= (1/C_{load})^*(i_{stim}{}^*R_{load}{}^*C_{load} - x^*R_{load}{}^*C_{load} + i_{stim}{}^*pw_1 + x^*pw_1 + i_{stim}{}^*pw_2 - x^*pw_2) +$$
$$(Istim^*pw_2)/C_{sc} - (x^*pw_2)/C_{sc}$$

Grouping x-terms from the above equation produces:

$$= x^*pw_1/C_{load} + x^*R_{load}{}^*C_{load}/C_{load} + x^*R_{load}{}^*C_{load}/C_{load} +$$
$$x^*pw_2/C_{load} + x^*pw_2/C_{sc} - x^*pw_1/C_{load}$$
$$= (1/C_{load})^*(x^*pw_1 + 2^*x^*R_{load}{}^*C_{load} + x^*pw_2 - x^*pw_1) +$$
$$x^*pw_2/C_{sc}$$

which leads to:

$$= (1/C_{load})^*(2^*x^*R_{load}{}^*C_{load} + x^*pw_2) + x^*pw_2/C_{sc}$$
$$= (1/C_{load})^*(i_{stim}{}^*R_{load}{}^*C_{load} + i_{stim}{}^*pw_1 + i_{stim}{}^*pw_2) -$$
$$1/C_{load}{}^*(i_{stim}{}^*R_{load}{}^*C_{load} + I_{stim}{}^*pw_1) +$$
$$i_{stim}{}^*pw_2/C_{sc},$$

and:

$$(1/Cload)^*(2^*x^*R_{load}{}^*C_{load} + x^*pw_2) + x^*pw_2/C_{sc} = (1/C_{load})^*(i_{stim}{}^*pw_2) + i_{stim}{}^*pw_2/C_{sc}$$

and:

$$2^*x^*R_{load}{}^*C_{load} x^*pw_2 + x^*pw_2{}^*C_{load}/C_{sc} = i_{stim}{}^*pw_2{}^*C_{load}/C_{sc}$$

and then:

$$x*(2*R_{load}*C_{load}+pw_2+pw_2*C_{load}/C_{sc})=i_{stim}*pw_2+i_{stim}*pw_2*C_{load}/C_{sc}$$

and finally:

$$x=(i_{stim}*pw_2+(i_{stim}*pw_2*C_{load})/C_{sc})/(2*R_{load}*C_{load}+pw_2+(pw_2*C_{load}/C_{sc}))$$

To determine the most efficient way to split a pulse into two amplitudes while maintaining the same average current (assuming $pw_1=pw_2$), the delta amplitude x can therefore be computed as follows:

$$x=(i_{stim}*pw_2+(i_{stim}*pw_2*C_{load})/C_{sc})/(2*R_{load}*C_{load}+pw_2+(pw_2*C_{load}/C_{sc})).$$

Using the value of x, the pulse current levels $i_{stim1}$ an $i_{stim2}$ for the first and second sub-pulses, respectively, can be computed as:

$$=i_{stim1}=i_{stim}+x, \text{ and}$$

$$=i_{stim2}-i_{stim}-x$$

In the above equations, $i_{stim1}$ is the pulse current level for the first sub-pulse $Stim_1$, $i_{stim2}$ is the pulse current level for the second sub-pulse $Stim_2$, $i_{stim}$ is the programmed current value for a pulse Stim and the average stimulation current to be delivered for the pulse when split into two sub-pulses $Stim_1$ and $Stim_2$ of equal pulse width, $pw_1$ is the pulse width of the first sub-pulse, $pw_2$ is the pulse width of the second sub-pulse, $C_{load}$ is the effective load capacitance of the electrode-tissue load driven by a given current regulator, $C_{sc}$ is the effective capacitance of the voltage supply capacitor, and $R_{load}$ is the effective load resistance of the electrode-tissue load driven by the given current regulator via selected electrodes. For a given current regulator, an electrode coupled to the regulator may source or sink regulated current that is applied to the tissue. At least a portion of the source current delivered by an electrode will then be sunk by one or more other electrodes in a selected electrode combination, functioning either as regulated sink electrodes or unregulated sink electrodes. Similarly, at least a portion of the sink current handled by an electrode will be sourced by one or more other electrodes in a selected electrode combination, functioning either as regulated source electrodes or unregulated source electrodes.

With a constant current pulse output, the discharge of the supply capacitor typically will be linear as long as the current remains constant. When the current is delivered in a split pulse, with first and second sub-pulses at different current levels, the discharge slope of the supply capacitor changes, but a 50/50 split appears to be optimum. In particular, an equidistant division of the sub-pulses such that the first sub-pulse width $pw_1$ is equal to the second sub-pulse width $pw_2$ may be a good practical option. However, the delivery of sub-pulses with different pulse widths also may be useful. In each case, whether equal or nonequal pulse widths are used, the current levels of the pulse widths can be selected to deliver a desired average current pulse level.

If a defined pulse is specified to have a current level of Istim over a pulse width of pw, values of Istim1 (Istim+x) and Istim2 (Istim−x) over first and second sub-pulse widths of pw/2 each, can be computed for a given initial voltage supply level, supply capacitance, load capacitance, load resistance, and headroom voltage, which can be predetermined by measurement, using the equations to solve for x, as presented above. In this manner, the sub-pulses and associated current levels specify the decay profile for the pulse during the pulse width such that the pulse voltage level does not exceed the supply voltage level of the current regulator.

As an illustration, a clinician programmer 40 may permit a clinician to define programs for transmission to stimulator 34 to control delivery of electrical stimulation therapy. Clinician programmer 40 may receive pulse parameters from the clinician, such as pulse current level (Istim), pulse rate, pulse width (pw), and electrode configuration. Using the parameters provided by the clinician, clinician programmer 40 may define a split pulse having first and second sub-pulses that provide an average pulse current level, over the pulse width, that approximates the pulse current level Istim specified by the clinician. In particular, processor 53 within clinician programmer 40 may automatically solve for x using the equations above, given measured or otherwise known values of the other parameters in the equations (such as $i_{stim}$, $V_{sc}$, $V_H$, $C_{load}$, $C_{sc}$, $R_{load}$, and $C_{load}$), and thereby produce values for Istim1 (computed as Istim+x) and Istim2 (computed as Istim−x). In some examples, clinician programmer 40 may be configured to select equal values for the sub-pulse widths such that $pw_1=pw_2$. Clinician programmer 40 then may modify the program to indicate the calculated sub-pulse current levels and pulse widths for each pulse to be split. The program can be transmitted from clinician programmer 40 to stimulator 34 to control delivery of split pulses by the stimulator to ensure that the sum of the pulse voltage level and the headroom voltage does not exceed the actual supply voltage of the current regulator.

As an alternative to calculating the split-pulse parameters, in some examples, clinician programmer 40 may refer to a multi-dimensional lookup table that stores Istim1, Istim2, pw1 and pw2 for different combinations Istim and the other parameters. Hence, clinician programmer 40 may calculate the split-pulse values dynamically using equations similar to those above, or look up, in memory 55, pre-computed split-pulse values generated previously using equations similar to those above. As a further alternative, generation of the split-pulse parameters could be performed within other devices such as patient programmer 42 or a computer communicatively coupled to clinician programmer 40 or patient programmer 42.

As another alternative, generation of the split-pulse parameters could be performed within stimulator 34 instead of within an external programmer. For example, the program provided to stimulator 34 by clinician programmer 40 could be modified by stimulator 34, either by calculating split-pulse parameters dynamically using equations similar to those above, or looking up, in memory 52, pre-computed split-pulse values generated previously using equations similar to those above. Also, in some cases, if a patient adjusts the pulse current level using patient programmer 42, the patient programmer or stimulator 34 may make necessary adjustments to the split-pulse parameters based on the current level adjustment.

The split-pulse or other decaying pulse technique may be entirely transparent to the clinician via clinician programmer 40 such that the clinician programmer presents the sub-pulse parameters to the clinician. Alternatively, the clinician programmer 40 may only present the pulse current level of a single pulse specified by the clinician, and not expose to the clinician the sub-pulse current level values that support delivery of an average pulse current level that is approximately equal to the specified pulse current level via sub-pulses. In this case, the clinician may define programs in terms of pulses, while the programmer 40 or stimulator 34 translate the pulses into sub-pulses. In other cases, the clinician may directly select the sub-pulse parameters.

Figure 12A:
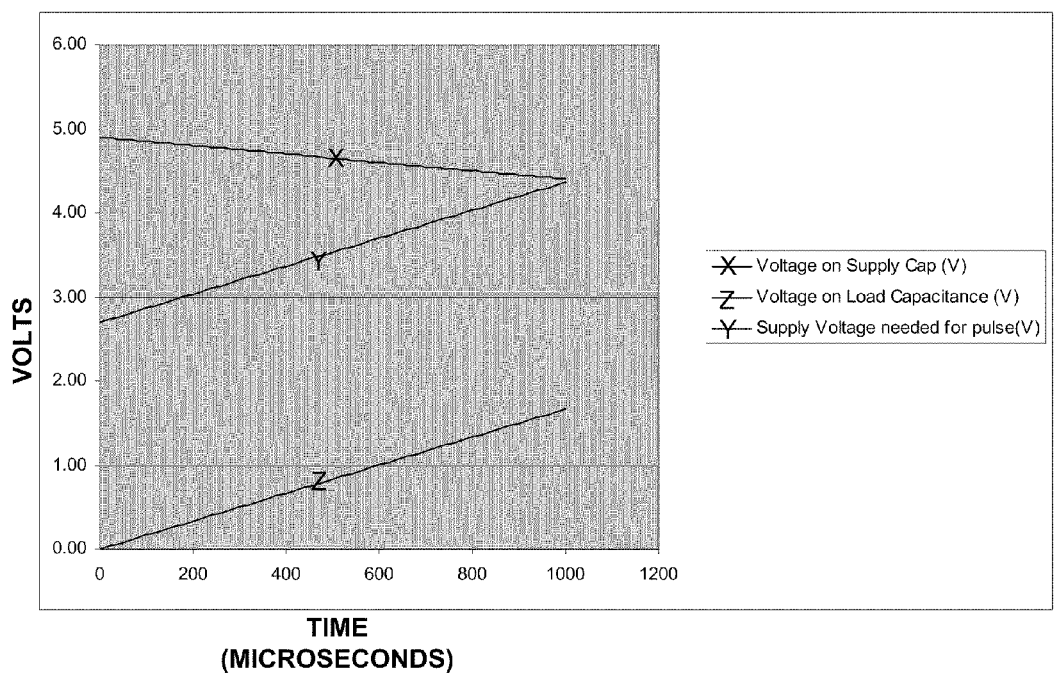
FIGS. 12A-12C are graphs illustrating performance results for different pulse configurations.
Figure 12B:
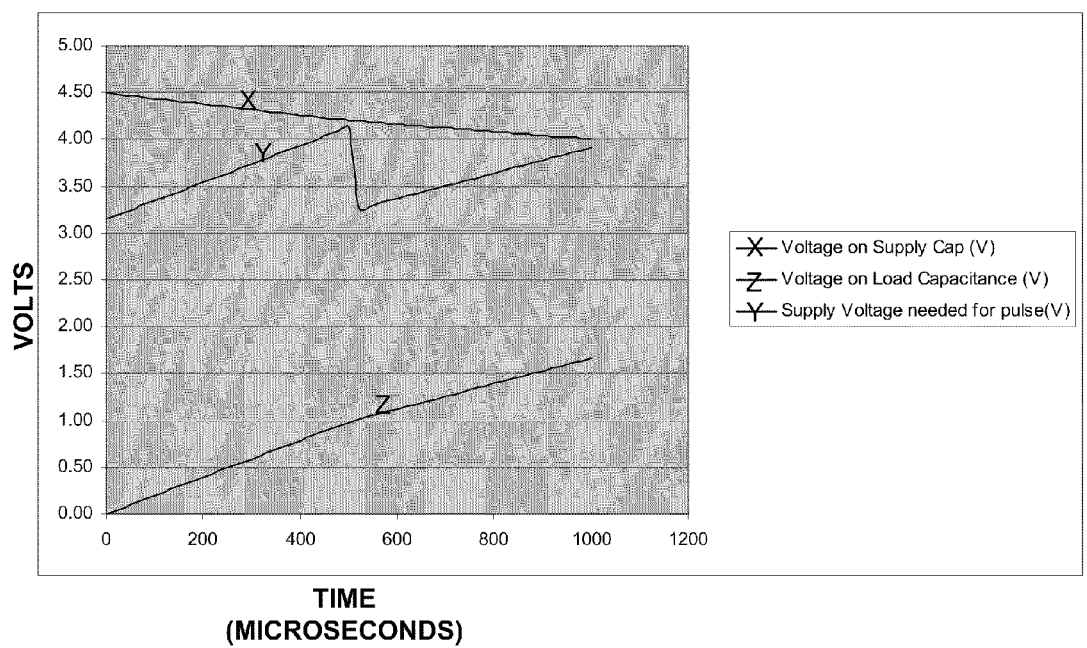
Figure 12C:
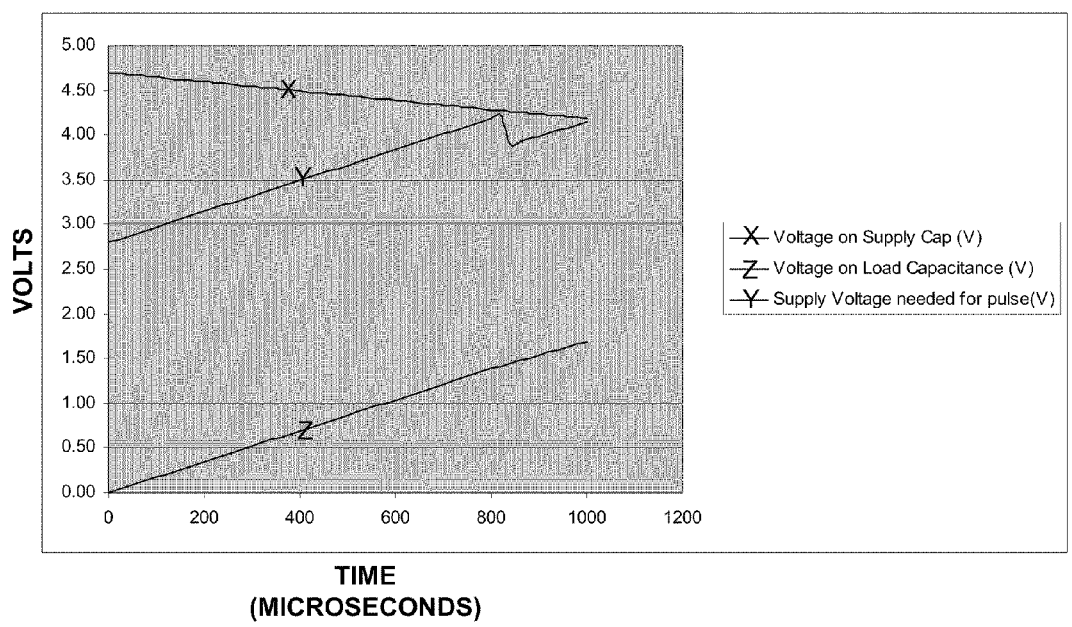

Set forth below are three examples illustrating (1) delivery of a stimulation current pulse with a constant pulse current level, (2) delivery of two sub-pulses with equal pulse widths but different pulse current levels to deliver an average current that is approximately equal to the constant pulse current level of (1), and (3) delivery of two sub-pulses with nonequal pulse widths and different pulse current levels to deliver an average current that is approximately equal to the constant pulse current level of (1). FIGS. 12A-12C are graphs illustrating performance results for the three different pulse configurations (1)-(3).

In a simulation for the first example (1), for a constant current pulse, a programmed constant pulse current level $I_{stim}$ was specified to be 5 mA, the voltage supply capacitor size was 10 microfarads, the effective load capacitance was 3 microfarads, the load impedance was 500 ohms, the starting voltage $V_{sc}$ of the supply capacitor was 4.9 volts, and the headroom needed for delivery of a regulated current pulse was 0.2 volts. Over a pulse width of 1000 microseconds, as the pulse was delivered at a constant pulse current of 5 mA, the charge on the supply capacitor dropped from 49.00 microcoulombs at time=0 to 44.00 microcoulombs at time=1000 microseconds.

The voltage on the supply capacitor for example (1) dropped from 4.9 volts at time=0 to 4.4 volts at time=1000 microseconds. The voltage on the load capacitance increased from 0.00 volts at time=0 to 1.67 volts at time=1000 microseconds. From time=0 to time=1000 microseconds, the supply voltage needed to maintain adequate headroom with respect to the pulse voltage increased from 2.7 volts to 4.37 volts. FIG. 12A illustrates the performance results for this first example (1). Traces X, Y and Z indicate the voltage on the supply capacitor ($V_{sc}$), the supply voltage required to deliver the regulated current pulse, and the voltage on the load capacitance, respectively, over the course of an example 1000 microsecond pulse width, for a single constant current pulse. The supply voltage Y required to deliver the regulated current pulse is approximately the sum of the pulse voltage level and the headroom voltage for the current regulator. As shown in FIG. 12A, the required supply voltage Y remains below the actual supply voltage X during the pulse width.

In a simulation for the second example (2), for a current pulse formed by first and second sub-pulses with equal pulse widths, an average pulse current level $I_{stim}$ was specified to be 5 mA, the voltage supply capacitor size was 10 microfarads, the effective load capacitance was 3 microfarads, the load impedance was 500 ohms, the starting voltage $V_{sc}$ of the supply capacitor was 4.5 volts, and the headroom needed for delivery of a regulated current pulse was 0.2 volts. In this example, the programmed current level for the first sub-pulse was 5.9 mA and the programmed current level for the second sub-pulse was 4.1 mA. In this case, the delta x value was 0.9 mA. Accordingly, with Istim=5.0, Istim1 was equal to 5.0+0.9=5.9 mA, and Istim2 was equal to 5.0−0.9=4.1 mA. Over a first sub-pulse width of 500 microseconds, as the sub-pulse was delivered at a constant pulse current of 5.9 mA, the charge on the supply capacitor dropped from 45.00 microcoulombs at time=0 to 42.05 microcoulombs at time=500 microseconds. Over a second sub-pulse width of 500 microseconds, as the sub-pulse was delivered at a constant pulse current of 4.1 mA, the charge on the supply capacitor dropped from 41.97 microcoulombs at 520 microseconds to 40.00 microcoulombs at time=1000 microseconds.

The voltage on the supply capacitor for example (2) dropped from 4.5 volts at time=0 to 4.2 volts at time=500 microseconds, and from 4.2 volts at time=520 microseconds to 4.00 volts at time=1000 microseconds. The voltage on the load capacitance increased from 0.00 volts at time=0 to 0.98 volts at time=500 microseconds, and from 1.01 volts at time=520 microseconds to 1.67 volts at time=1000 microseconds. From time=0 to time=500 microseconds, the supply voltage needed to maintain adequate headroom with respect to the pulse voltage increased from 3.15 volts to 4.13 volts. From time=520 microseconds to time=1000 microseconds, the supply voltage needed to maintain adequate headroom with respect to the pulse voltage increased from 3.26 volts to 3.92 volts. Notably, the required supply voltage at 520 microseconds, after the start of the second sub-pulse, was less than the required supply voltage at 500 microseconds, at the end of the first sub-pulse. FIG. 12B illustrates the performance results for this second example (2). Traces X, Y and Z indicate the voltage on the supply capacitor ($V_{sc}$), the supply voltage required to deliver the regulated current pulse, and the voltage on the load capacitance, respectively, over the course of an example 1000 microsecond pulse width, for a pulse divided into sub-pulses with equal pulse widths. The supply voltage required to deliver the regulated current pulse is approximately the sum of the pulse voltage level and the headroom voltage for the current regulator. As shown in FIG. 12B, the required supply voltage Y remains below the actual supply voltage X during the pulse width.

In a simulation for the third example (3), for a current pulse formed by first and second sub-pulses with nonequal pulse widths, an average pulse current level $I_{stim}$ was specified to be 5.074 mA, the voltage supply capacitor size was 10 microfarads, the effective load capacitance was the voltage supply capacitor size was 10 microfarads, the effective load capacitance was 3 microfarads, the load impedance was 500 ohms, the starting voltage $V_{sc}$ of the supply capacitor was 4.7 volts, and the headroom needed for delivery of a regulated current pulse was 0.2 volts. In this example, the programmed current level for the first sub-pulse was 5.2 mA and the programmed current level for the second sub-pulse was 4.5 mA. The first sub-pulse width was 820 microseconds, and the second sub-pulse width was 180 microseconds. Over the first sub-pulse width of 820 microseconds, as the sub-pulse was delivered at a constant pulse current of 5.2 mA, the charge on the supply capacitor dropped from 47.00 microcoulombs at time=0 to 42.74 microcoulombs at time=820 microseconds. Over the second sub-pulse width of 180 microseconds, as the sub-pulse was delivered at a constant pulse current of 4.5 mA, the charge on the supply capacitor dropped from 42.65 microcoulombs at 840 microseconds to 41.93 microcoulombs at time=1000 microseconds.

The voltage on the supply capacitor for example (3) dropped from 4.7 volts at time=0 to 4.27 volts at time=820 microseconds, and from 4.26 volts at time=840 microseconds to 4.19 volts at time=1000 microseconds. The voltage on the load capacitance increased from 0.00 volts at time=0 to 1.42 volts at time=820 microseconds, and from 1.45 volts at time=840 microseconds to 1.69 volts at time=1000 microseconds. From time=0 to time=820 microseconds, the supply voltage needed to maintain adequate headroom with respect to the pulse voltage increased from 2.80 volts to 4.22 volts. From time=840 microseconds to time=1000 microseconds, the supply voltage needed to maintain adequate headroom with respect to the pulse voltage increased from 3.90 volts to 4.14 volts. Notably, the required supply voltage at 840 microseconds, after the start of the second sub-pulse, was less than the required supply voltage at 820 microseconds, at the end of the first sub-pulse. FIG. 12C illustrates the performance results for this third example (3). Traces X, Y and Z indicate the voltage on the supply capacitor ($V_{sc}$), the supply voltage required to deliver the regulated current pulse, and the voltage on the load capacitance, respectively, over the course of an example 1000 microsecond pulse width, for a pulse divided into sub-pulses with nonequal pulse widths. The supply voltage required to deliver the regulated current pulse is approximately the sum of the pulse voltage level and the headroom voltage for the current regulator. As shown in FIG. 12C, the required supply voltage Y remains below the actual supply voltage X during the pulse width.

The techniques and components described in this disclosure may be implemented, at least in part, in hardware, software, firmware or any combination thereof. Electrical circuit components may be formed, for example, by integrated and/or discrete devices fabricated using any of a variety of conventional processes generally used for electrical circuitry provided in medical devices, such as implantable medical devices. Various control features may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. In this disclosure, the terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various aspects of the disclosure have been described. These and other aspects are within the scope of the following claims.

The invention claimed is:

1. A method for delivery of electrical stimulation, the method comprising:
   generating, with a current regulator, an electrical stimulation pulse having a pulse current level, a pulse voltage level, and a pulse width;
   controlling the pulse current level to decrease during the pulse width such that a sum of the pulse voltage level and a headroom voltage level requirement of the current regulator does not exceed a supply voltage level; and
   delivering the pulse via one or more implantable electrodes.

2. The method of claim 1, wherein controlling comprises controlling the pulse current level to decrease based at least in part on a decrease in the supply voltage level during the pulse width.

3. The method of claim 2, wherein controlling comprises controlling the pulse current level to decrease based at least in part on the decrease in the supply voltage level and an increase in a load voltage during the pulse width.

4. The method of claim 1, wherein generating an electrical stimulation pulse comprises generating an electrical stimulation pulse having first and second sub-pulses, the second sub-pulse following the first sub-pulse in time, wherein the pulse current level of the second sub-pulse is less than the pulse current level of the first sub-pulse.

5. The method of claim 4, wherein an average of the pulse current level during the first and second sub-pulses is selected such that the sum of the pulse voltage level and the headroom voltage level requirement does not exceed the supply voltage level.

6. The method of claim 4, wherein the first and second sub-pulses have equal sub-pulse widths.

7. The method of claim 6, wherein the first and second sub-pulses have unequal sub-pulse widths.

8. The method of claim 1, wherein the pulse voltage level increases during the pulse width and the supply voltage level decreases during the pulse width.

9. The method of claim 1, wherein generating comprises generating a plurality of pulses.

10. The method of claim 1, wherein controlling comprises controlling the pulse current level according to data stored in memory of at least one of an implantable medical device comprising the current regulator or an external programmer that communicates with the implantable medical device.

11. A medical device for delivery of electrical stimulation, the device comprising:
   a stimulation pulse generator comprising a current regulator configured to generate an electrical stimulation pulse having a pulse current level, a pulse voltage level, and a pulse width;
   a controller configured to control the pulse current level to decrease during the pulse width such that a sum of the pulse voltage level and a headroom voltage level requirement of the current regulator does not exceed a supply voltage level; and
   one or more implantable electrodes configured to deliver the pulse.

12. The device of claim 11, wherein the controller is configured to control the pulse current level to decrease based at least in part on a decrease in the supply voltage level during the pulse width.

13. The device of claim 12, wherein the controller is configured to control the pulse current level to decrease based at least in part on the decrease in the supply voltage level and an increase in a load voltage during the pulse width.

14. The device of claim 11, wherein the stimulation pulse generator is configured to generate the electrical stimulation pulse to have first and second sub-pulses, the second sub-pulse following the first sub-pulse in time, wherein the pulse current level of the second sub-pulse is less than the pulse current level of the first sub-pulse.

15. The device of claim 14, wherein an average of the pulse current level during the first and second sub-pulses is selected such that the sum of the pulse voltage level and the headroom voltage level requirement does not exceed the supply voltage level.

16. The device of claim 14, wherein the first and second sub-pulses have equal sub-pulse widths.

17. The device of claim 14, wherein the first and second sub-pulses have unequal sub-pulse widths.

18. The device of claim 11, wherein the pulse voltage level increases during the pulse width and the supply voltage level decreases during the pulse width.

19. The device of claim 11, wherein the stimulation pulse generator is configured to generate a plurality of pulses.

20. The device of claim 11, wherein the controller is configured to control the pulse current level according to data stored in memory of at least one of the medical device or an external programmer that communicates with the medical device.

21. A medical device for delivery of electrical stimulation, the device comprising:

means for generating an electrical stimulation pulse having a pulse current level, a pulse voltage level, and a pulse width;

means for controlling the pulse current level to decrease during the pulse width such that a sum of the pulse voltage level and a headroom voltage level requirement of the generating means does not exceed a supply voltage level; and means for delivering the pulse via one or more implantable electrodes.

22. The device of claim 21, wherein the means for controlling comprises means for controlling the pulse current level to decrease based at least in part on a decrease in the supply voltage level during the pulse width.

23. The device of claim 22, wherein the means for controlling comprises means for controlling the pulse current level to decrease based at least in part on the decrease in the supply voltage level and an increase in a load voltage during the pulse width.

24. The device of claim 21, wherein the means for generating an electrical stimulation pulse comprises means for generating an electrical stimulation pulse having first and second sub-pulses, the second sub-pulse following the first sub-pulse in time, wherein the pulse current level of the second sub-pulse is less than the pulse current level of the first sub-pulse.

25. The device of claim 24, wherein an average of the pulse current level during the first and second sub-pulses is selected such that the sum of the pulse voltage level and the headroom voltage level requirement does not exceed the supply voltage level.

26. The device of claim 24, wherein the first and second sub-pulses have equal sub-pulse widths.

27. The device of claim 24, wherein the first and second sub-pulses have unequal sub-pulse widths.

28. The device of claim 21, wherein the pulse voltage level increases during the pulse width and the supply voltage level decreases during the pulse width.

29. The device of claim 21, wherein the means for generating comprise means for generating a plurality of pulses.

30. The device of claim 21, wherein the means for controlling comprises means for controlling the pulse current level according to data stored in memory of at least one of an implantable medical device comprising the current regulator or an external programmer that communicates with the implantable medical device.

* * * * *